United States Patent [19]
Christensen, IV et al.

[11] Patent Number: 5,811,455
[45] Date of Patent: *Sep. 22, 1998

[54] COMPOUNDS USEFUL FOR TREATING ALLERGIC OR INFLAMMATORY DISEASES

[75] Inventors: Siegfried Benjamin Christensen, IV, Philadelphia, Pa.; Paul Elliot Bender, Cherry Hill, N.J.; Cornelia Jutta Forster, Bensalem, Pa.

[73] Assignee: SmithKline Beecham Corporation, Philadelphia, Pa.

[ * ] Notice: The term of this patent shall not extend beyond the expiration date of Pat. No. 5,449,686.

[21] Appl. No.: 488,556

[22] Filed: May 24, 1995

Related U.S. Application Data

[63] Continuation of Ser. No. 313,095, Sep. 12, 1994, Pat. No. 5,449,686, which is a continuation of PCT/US93/02325 Mar. 12, 1993, which is a continuation-in-part of PCT/US93/02045 Mar. 5, 1993, which is a continuation-in-part of Ser. No. 968,753, Oct. 30, 1992, abandoned, which is a continuation-in-part of Ser. No. 862,083, Apr. 2, 1992, abandoned.

[51] Int. Cl.$^6$ ........................ A61K 31/275; C07C 255/46
[52] U.S. Cl. .................. 514/520; 514/521; 514/523; 558/426; 558/430
[58] Field of Search ..................... 558/426, 430; 514/520, 521, 523

[56] References Cited

U.S. PATENT DOCUMENTS 3,759,974  9/1973  Treiber et al. ..................... 558/426

OTHER PUBLICATIONS

Chemical Abstracts vol. 90, 1979, Abstract 90:86895p.

*Primary Examiner*—Fiona T. Powers
*Attorney, Agent, or Firm*—James M. Kanagy; Stephen Venetianer; Edward T. Lentz

[57] ABSTRACT

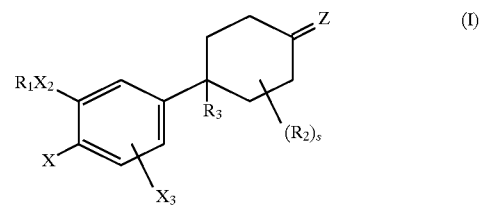

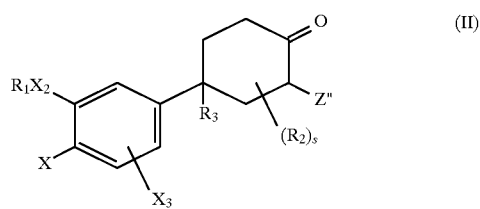

Novel cyclohexanes of formulas (I) and (II) are described herein. They inhibit the production of Tumor Necrosis Factor and are useful in the treatment of disease states mediated or exacerbated by TNF production; these compounds are also useful in the mediation or inhibition of enzymatic or catalytic activity of phosphodiesterase IV.

10 Claims, No Drawings

COMPOUNDS USEFUL FOR TREATING ALLERGIC OR INFLAMMATORY DISEASES

This application is a continuation of U.S. Ser. No. 08/313,095 filed 12 Sep., 1994, now U.S. Pat. No. 5,449,686; which is a national stage application of PCT/US93/02325 filed 12 Mar. 1993, now abandoned; which is a continuation-in-part of PCT/US93/02045 filed 5 Mar., 1993, now abandoned; which is a continuation-in-part of U.S. Ser. No. 07/968,753 filed 30 Oct., 1992, now abandoned; which is a continuation-in-part of U.S. Ser. No. 07/862,083 filed 2 Apr., 1992, now abandoned.

FIELD OF INVENTION

The present invention relates to novel compounds, pharmaceutical compositions containing these compounds, and their use in treating allergic and inflammatory diseases and for inhibiting the production of Tumor Necrosis Factor (TNF).

BACKGROUND OF THE INVENTION

Bronchial asthma is a complex, multifactorial disease characterized by reversible narrowing of the airway and hyperreactivity of the respiratory tract to external stimuli.

Identification of novel therapeutic agents for asthma is made difficult by the fact that multiple mediators are responsible for the development of the disease. Thus, it seems unlikely that eliminating the effects of a single mediator will have a substantial effect on all three components of chronic asthma. An alternative to the "mediator approach" is to regulate the activity of the cells responsible for the pathophysiology of the disease.

One such way is by elevating levels of cAMP (adenosine cyclic 3',5'-monophosphate). Cyclic AMP has been shown to be a second messenger mediating the biologic responses to a wide range of hormones, neurotransmitters and drugs; [Krebs Endocrinology Proceedings of the 4th International Congress Excerpta Medica, 17–29, 1973]. When the appropriate agonist binds to specific cell surface receptors, adenylate cyclase is activated, which converts $Mg^{+2}$-ATP to cAMP at an accelerated rate.

Cyclic AMP modulates the activity of most, if not all, of the cells that contribute to the pathophysiology of extrinsic (allergic) asthma. As such, an elevation of cAMP would produce beneficial effects including: 1) airway smooth muscle relaxation, 2) inhibition of mast cell mediator release, 3) suppression of neutrophil degranulation, 4) inhibition of basophil degranulation, and 5) inhibition of monocyte and macrophage activation. Hence, compounds that activate adenylate cyclase or inhibit phosphodiesterase should be effective in suppressing the inappropriate activation of airway smooth muscle and a wide variety of inflammatory cells. The principal cellular mechanism for the inactivation of cAMP is hydrolysis of the 3'-phosphodiester bond by one or more of a family of isozymes referred to as cyclic nucleotide phosphodiesterases (PDEs).

It has now been shown that a distinct cyclic nucleotide phosphodiesterase (PDE) isozyme, PDE IV, is responsible for cAMP breakdown in airway smooth muscle and inflammatory cells. [Torphy, "Phosphodiesterase Isozymes: Potential Targets for Novel Anti-asthmatic Agents" in New Drugs for Asthma, Barnes, ed IBC Technical Services Ltd., 1989]. Research indicates that inhibition of this enzyme not only produces airway smooth muscle relaxation, but also suppresses degranulation of mast cells, basophils and neutrophils along with inhibiting the activation of monocytes and neutrophils. Moreover, the beneficial effects of PDE IV inhibitors are markedly potentiated when adenylate cyclase activity of target cells is elevated by appropriate hormones or autocoids, as would be the case in vivo. Thus PDE IV inhibitors would be effective in the asthmatic lung, where levels of prostaglandin $E_2$ and prostacyclin (activators of adenylate cyclase) are elevated. Such compounds would offer a unique approach toward the pharmacotherapy of bronchial asthma and possess significant therapeutic advantages over agents currently on the market.

The compounds of this invention also inhibit the production of Tumor Necrosis Factor (TNF), a serum glycoprotein. Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft vs. host reaction, allograft rejections, fever and myalgias due to infection, such as influenza, cachexia secondary to infection or malignancy, cachexia secondary to human acquired immune deficiency syndrome (AIDS), AIDS, ARC (AIDS related complex), keloid formation, scar tissue formation, Crohn's disease, ulcerative colitis, or pyresis, in addition to a number of autoimmune diseases, such as multiple sclerosis, autoimmune diabetes and systemic lupus erythematosis.

AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell-mediated immunity is impaired and infected individuals manifest severe opportunistic infections and/or unusual neoplasms. HIV entry into the T lymphocyte requires T lymphocyte activation. Viruses such as HIV-1 or HIV-2 infect T lymphocytes after T cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication.

Cytokines, specifically TNF, are implicated in activated T-cell-mediated HIV protein expression and/or virus replication by playing a role in maintaining T lymphocyte activation. Therefore, interference with cytokine activity such as by inhibition of cytokine production, notably TNF, in an HIV-infected individual aids in limiting the maintenance of T cell activation, thereby reducing the progression of HIV infectivity to previously uninfected cells which results in a slowing or elimination of the progression of immune dysfunction caused by HIV infection. Monocytes, macrophages, and related cells, such as kupffer and glial cells, have also been implicated in maintenance of the HIV infection. These cells, like T cells, are targets for viral replication and the level of viral replication is dependent upon the activation state of the cells. [See Rosenberg et al., The Immunopathogenesis of HIV Infection, Advances in Immunology, Vol. 57, 1989]. Monokines, such as TNF, have been shown to activate HIV replication in monocytes and/or macrophages [See Poli et al., Proc. Natl. Acad. Sci., 87:782–784, 1990], therefore, inhibition of monokine production or activity aids in limiting HIV progression as stated above for T cells.

TNF has also been implicated in various roles with other viral infections, such as the cytomegalovirus (CMV), influenza virus, adenovirus, and the herpes virus for similar reasons as those noted.

TNF is also associated with yeast and fungal infections. Specifically *Candida albicans* has been shown to induce TNF production in vitro in human monocytes and natural killer cells. [See Riipi et al., Infection and Immunity, 58(9):2750–54, 1990; and Jafari et al., Journal of Infectious Diseases, 164:389–95, 1991. See also Wasan et al., Antimicrobial Agents and Chemotherapy, 35, (10):2046–48, 1991; and Luke et al., Journal of Infectious Diseases, 162:211–214, 1990].

The ability to control the adverse effects of TNF is furthered by the use of the compounds which inhibit TNF in mammals who are in need of such use. There remains a need for compounds which are useful in treating TNF-mediated disease states which are exacerbated or caused by the excessive and/or unregulated production of TNF.

SUMMARY OF THE INVENTION

This invention relates to the novel compounds of Formulas (I) and (II) as shown below, useful in the mediation or inhibition of the enzymatic activity (or catalytic activity) of phosphodiesterase IV (PDE IV). These compounds also have Tumor Necrosis Factor (TNF) inhibitory activity.

This invention also relates to the pharmaceutical compositions comprising a compound of Formulas (I) or (II) and a pharmaceutically acceptable carrier or diluent.

The invention also relates to a method of mediation or inhibition of the enzymatic activity (or catalytic activity) of PDE IV in mammals, including humans, which comprises administering to a mammal in need thereof an effective amount of a compound of Formula (I) or (II) as shown below.

The invention further provides a method for the treatment of allergic and inflammatory disease which comprises administering to a mammal, including humans, in need thereof, an effective amount of a compound of Formula (I) or (II).

The invention also provides a method for the treatment of asthma which comprises administering to a mammal, including humans, in need thereof, an effective amount of a compound of Formula (I) or (II).

This invention also relates to a method of inhibiting TNF production in a mammal, including humans, which method comprises administering to a mammal in need of such treatment, an effective TNF inhibiting amount of a compound of Formula (I) or (II). This method may be used for the prophylactic treatment or prevention of certain TNF mediated disease states amenable thereto.

This invention also relates to a method of treating a human afflicted with a human immunodeficiency virus (HIV), which comprises administering to such human an effective TNF inhibiting amount of a compound of Formula (I) or (II).

Compounds of Formula (I) or (II) are also useful in the treatment of additional viral infections, where such viruses are sensitive to upregulation by TNF or will elicit TNF production in vivo.

In addition, compounds of Formula ( I) or (II) are also useful in treating yeast and fungal infections, where such yeast and fungi are sensitive to upregulation by TNF or will elicit TNF production in vivo.

Certain novel compounds of this invention are represented by Formula (I):

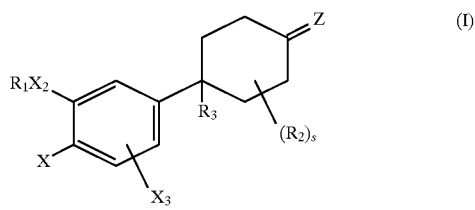

wherein:
$R_1$ is $-(CR_4R_5)_nC(O)O(CR_4R_5)_mR_6$, $-(CR_4R_5)_nC(O)NR_4(CR_4R_5)_mR_6$, $-(CR_4R_5)_nO(CR_4R_5)_mR_6$, or $-(CR_4R_5)_rR_6$ wherein the alkyl moieties may be optionally substituted with one or more halogens;
m is 0 to 2;
n is 1 to 4;
r is 1 to 6;
$R_4$ and $R_5$ are independently selected hydrogen or $C_{1-2}$ alkyl;
$R_6$ is hydrogen, methyl, hydroxyl, aryl, halo substituted aryl, aryloxy$C_{1-3}$ alkyl, halo substituted aryloxy$C_{1-3}$ alkyl, indanyl, indenyl, $C_{7-11}$ polycycloalkyl, tetrahydrofuranyl, furanyl, tetrahydropyranyl, pyranyl, tetrahydrothienyl, thienyl, tetrahydrothiopyranyl, thiopyranyl, $C_{3-6}$ cycloalkyl, or a $C_{4-6}$ cycloalkyl containing one or two unsaturated bonds, wherein the cycloalkyl and heterocyclic moieties may be optionally substituted by 1 to 3 methyl groups or one ethyl group;
provided that:
a) when $R_6$ is hydroxyl, then m is 2; or
b) when $R_6$ is hydroxyl, then r is 2 to 6; or
c) when $R_6$ is 2-tetrahydropyranyl, 2-tetrahydrothiopyranyl, 2-tetrahydrofuranyl, or 2-tetrahydrothienyl, then m is 1 or 2; or
d) when $R_6$ is 2-tetrahydropyranyl, 2-tetrahydrothiopyranyl, 2-tetrahydrofuranyl, or 2-tetrahydrothienyl, then r is 1 to 6;
e) when n is 1 and m is 0, then $R_6$ is other than H in $-(CR_4R_5)_nO(CR_4R_5)_mR_6$;
X is $YR_2$, halogen, nitro, $NR_4R_5$, or formyl amine;
Y is O or $S(O)_{m'}$;
m' is 0, 1, or 2;
$X_2$ is O or $NR_8$;
$X_3$ is hydrogen or X;
$R_2$ is independently selected from $-CH_3$ or $-CH_2CH_3$ optionally substituted by 1 or more halogens;
s is 0 to 4;
$R_3$ is hydrogen, halogen, $C_{1-4}$ alkyl, halo-substituted $C_{1-4}$ alkyl, $CH_2NHC(O)C(O)NH_2$, $-CH=CR_8'R_8'$, cyclopropyl optionally substituted by $R_{8'}$, $_{CN,\ OR8}$, $CH_2OR_8$, $NR_8R_{10}$, $CH_2NR_8R_{10}$, $C(Z')H$, $C(O)OR_8$, $C(O)NR_8R_{10}$, or $C\equiv CR_{8'}$;
Z' is O, $NR_9$, $NOR_8$, NCN, $C(-CN)_2$, $CR_8CN$, $CR_8NO_2$, $CR_8C(O)OR_8$, $CR_8C(O)NR_8R_8$, $C(-CN)NO_2$, $C(-CN)C(O)OR_9$, or $C(-CN)C(O)NR_8R_8$;
Z is O, $NR_7$, $NCR_4R_5C_{2-6}$ alkenyl, $NOR_{14}$, $NOR_{15}$, $NOCR_4R_5C_{2-6}$ alkenyl, $NNR_4R_{14}$, $NNR_4R_{15}$, NCN, $NNR_8C(O)NR_8R_{14\ NNR8}C(S)NR_8R_{14}$, or =Z is 2-(1,3-dithiane), 2-(1,3-dithilolane), dimethylthio ketal, diethylthio ketal, 2-(1,3-dioxolane), 2(1,3-dioxane), 2-(1,3-oxathiolane), dimethyl ketal or diethy ketal;
$R_7$ is $-(CR_4R_5)_qR_{12}$ or $C_{1-6}$ alkyl wherein the $R_{12}$ or $C_{1-6}$ alkyl group is optionally substituted one or more times by $C_{1-2}$ alkyl optionally substituted by one to three fluorines, —F, —Br, —Cl, —NO$_2$, —Si(R$_4$)$_3$, —NR$_{10}$R$_{11}$, —C(O)R$_8$, —CO$_2$R$_8$, —OR$_8$, —CN, —C(O)NR$_{10}$R$_{11}$, —OC(O)NR$_{10}$R$_{11}$, —OC(O)R$_8$, —NR$_{10}$C(O)NR$_{10}$R$_{11}$, —NR$_{10}$C(O)R$_{11}$, —NR$_{10}$C(O)OR$_9$, —NR$_{10}$C(O)R$_{13}$, —C(NR$_{10}$)NR$_{10}$R$_{11}$, —C(NCN)NR$_{10}$R$_{11}$, —C(NCN)SR$_9$, —NR$_{10}$C(NCN)SR$_9$, —NR$_{10}$C(NCN)NR$_{10}$R$_{11}$, —NR$_{10}$S(O)$_2$R$_9$, —S(O)$_m$R$_9$, —NR$_{10}$C(O)C(O)NR$_{10}$R$_{11}$, —NR$_{10}$C(O)C(O)R$_{10}$, thiazolyl, imidazolyl, oxazolyl, pyrazolyl, triazolyl, or tetrazolyl;

q is 0, 1, or 2;

R$_{12}$ is C$_{3-7}$ cycloalkyl, (2-, 3- or 4-pyridyl), pyrimidyl, pyrazolyl, (1- or 2-imidazolyl), thiazolyl, triazolyl, pyrrolyl, piperazinyl, piperidinyl, morpholinyl, furanyl, (2- or 3-thienyl), (4- or 5-thienyl), quinolinyl, naphthyl, or phenyl;

R$_8$ is independently selected from hydrogen or R$_9$;

R$_{8'}$ is R$_8$ or fluorine;

R$_9$ is C$_{1-4}$ alkyl optionally substituted by one to three fluorines;

R$_{10}$ is OR$_8$ or R$_{11}$;

R$_{11}$ is hydrogen, or C$_{1-4}$ alkyl optionally substituted by one to three fluorines; or when R$_{10}$ and R$_{11}$ are as NR$_{10}$R$_{11}$ they may together with the nitrogen form a 5 to 7 membered ring optionally containing at least one additional heteroatom selected from O, N, or S;

R$_{13}$ is oxazolidinyl, oxazolyl, thiazolyl, pyrazolyl, triazolyl, tetrazolyl, imidazolyl, imidazolidinyl, thiazolidinyl, isoxazolyl, oxadiazolyl, or thiadiazolyl, and each of these heterocyclic rings is connected through a carbon atom and each may be unsubstituted or substituted by one or two C$_{1-2}$ alkyl groups;

R$_{14}$ is hydrogen or R$_7$; or when R$_8$ and R$_{14}$ are as NR$_8$R$_{14}$ they may together with the nitrogen form a 5 to 7 membered ring optionally containing one or more additional heteroatoms selected from O, N, or S;

R$_{15}$ is C(O)R$_{14}$, C(O)NR$_4$R$_{14}$, S(O)$_2$R$_7$, or S(O)$_2$NR$_4$R$_{14}$;

provided that:

(f) when Z is O, X is YR$_2$, Y is oxygen, X$_2$ is oxygen, X$_3$ is hydrogen, s is 0, R$_2$ is CH$_3$, and R$_1$ is CH$_3$, then R$_3$ is other than CN;

(g) when Z is O, X$_2$ is oxygen, X$_3$ is hydrogen, s is 0, and X is YR$_2$, then R$_3$ is other than hydrogen;

(h) when Z is N—O—CH$_2$CH=CH$_2$, X is YR$_2$, Y is oxygen, X$_2$ is oxygen, X$_3$ is hydrogen, s is 0, R$_2$ is CH$_3$, and R$_1$ is CH$_3$, then R$_3$ is other than CN;

(i) when R$_{12}$ is N-pyrazolyl, N-imidazolyl, N-triazolyl, N-pyrrolyl, N-piperazinyl, N-piperidinyl, or N-morpholinyl, then q is not 1; or (j) when Z is O or =Z is 2-(1,3-dioxolane) and R$_3$ is CH$_3$, CH$_2$OH or CH$_2$OC$_{1-4}$ alkyl then R$_1$X$_2$ is not C$_1$–C$_3$ alkoxy and X is not halogen, methoxy, ethoxy, methylthio, or ethylthio;

or the pharmaceutically acceptable salts thereof.

Another set of compounds of this invention are represented by Formula (II)

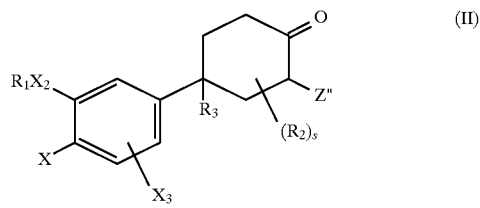

wherein:

R$_1$ is —(CR$_4$R$_5$)$_n$C(O)O(CR$_4$R$_5$)$_m$R$_6$, —(CR$_4$R$_5$)$_n$C(O)NR$_4$(CR$_4$R$_5$)$_m$R$_6$, —(CR$_4$R$_5$)$_n$O(CR$_4$R$_5$)$_m$R$_6$, or —(CR$_4$R$_5$)$_r$R$_6$ wherein the alkyl moieties may be optionally substituted with one or more halogens;

m is 0 to 2;

n is 1 to 4;

r is 1 to 6;

R$_4$ and R$_5$ are independently selected hydrogen or C$_{1-2}$ alkyl;

R$_6$ is hydrogen, methyl, hydroxyl, aryl, halo substituted aryl, aryloxyC$_{1-3}$ alkyl, halo substituted aryloxyC$_{1-3}$ alkyl, indanyl, indenyl, C$_{7-11}$ polycycloalkyl, tetrahydrofuranyl, furanyl, tetrahydropyranyl, pyranyl, tetrahydrothienyl, thienyl, tetrahydrothiopyranyl, thiopyranyl, C$_{3-6}$ cycloalkyl, or a C$_{4-6}$ cycloalkyl containing one or two unsaturated bonds, wherein the cycloalkyl and heterocyclic moieties is unsubstituted or substituted by 1 to 3 methyl groups or one ethyl group;

provided that:

a) when R$_6$ is hydroxyl, then m is 2; or b) when R$_6$ is hydroxyl, then r is 2 to 6; or c) when R$_6$ is 2-tetrahydropyranyl, 2-tetrahydrothiopyranyl, 2-tetrahydrofuranyl, or 2-tetrahydrothienyl, then m is 1 or 2; or d) when R$_6$ is 2-tetrahydropyranyl, 2-tetrahydrothiopyranyl, 2-tetrahydrofuranyl, or 2-tetrahydrothienyl, then r is 1 to 6;

e) when n is 1 and m is 0, then R$_6$ is other than H in —(CR$_4$R$_5$)$_n$O(CR$_4$R$_5$)$_m$R$_6$;

X is YR$_2$, halogen, nitro, NR$_4$R$_5$, or formyl amine;

Y is O or S(O)$_{m'}$;

m' is 0, 1, or 2;

X$_2$ is O or NR$_8$;

X$_3$ is hydrogen or X;

R$_2$ is independently selected from —CH$_3$ or —CH$_2$CH$_3$ optionally substituted by 1 or more halogens;

s is 0 to 4;

R$_3$ is hydrogen, halogen, C$_{1-4}$ alkyl, CH$_2$NHC(O)C(O)NH$_2$, halo-substituted C$_{1-4}$ alkyl, —CH=CR$_{8'}$, R$_{8'}$, cyclopropyl optionally substituted by R$_{8'}$, CN, OR$_8$, CH$_2$OR$_8$, NR$_8$R$_{10}$, CH$_2$NR$_8$R$_{10}$, C(Z')H, C(O)OR$_8$, C(O)NR$_8$R$_{10}$, or C≡CR$_{8'}$;

Z' is O, NR$_9$, NOR$_8$, NNR$_8$R$_8$, NCN, C(—CN)$_2$, CR$_8$CN, CR$_8$NO$_2$, CR$_8$C(O)OR$_9$, CR$_8$C(O)NR$_8$R$_8$, C(—CN)NO$_2$, C(—CN)C(O)OR$_9$, or C(—CN)C(O)NR$_8$R$_8$;

Z" is C(Y')R$_{14}$, C(O)OR$_{14}$, C(Y')NR$_{10}$R$_{14}$, C(NR$_{10}$)NR$_{10}$R$_{14}$, CN, C(NOR$_8$)R$_{14}$, C(O)NR$_8$NR$_8$C(O)R$_8$, C(O)NR$_8$NR$_{10}$R$_{14}$, C(NOR$_{14}$)R$_8$, C(NR$_8$)NR$_{10}$R$_{14}$, C(NR$_{14}$)NR$_8$R$_8$ C(NCN)NR$_{10}$R$_{14}$, C(NCN)SR$_9$, (2-, 4- or 5-imidazolyl), (3-, 4- or 5-pyrazolyl), (4- or 5-triazolyl[1,2,3]), (3- or 5-triazolyl[1,2,4]), (5-tetrazolyl), (2-, 4- or 5-oxazolyl), (3-, 4- or 5-isoxazolyl), (3- or 5-oxadiazolyl[1,2,4]), (2-oxadiazolyl[1,3,4]), (2-thiadiazolyl[1,3,4]), (2-, 4-, or 5-thiazolyl), (2-, 4, or 5-oxazolidinyl), (2-, 4-, or 5-thiazolidinyl), or (2-, 4-, or 5-imidazolidinyl); wherein all of the heterocylic ring systems may be optionally substituted one or more times by $R_{14}$;

Y' is O or S;

the remaining the substituents for compounds of Formula (II). including, $R_7$, q, $R_{12}$, $R_8$, $R_{8'}$, $R_9$, $R_{10}$, $R_{11}$, $R_{13}$, $R_{14}$, and $R_{15}$ have the same definitions given in regards to Formula (I), where applicable;

provided that:

f) when $R_{12}$ is N-pyrazolyl, N-imidazolyl, N-triazolyl, N-pyrrolyl, N-piperazinyl, N-piperidinyl, or N-morpholinyl, then q is not 1; or g) when Z" is C(O)$OR_{14}$ where $R_{14}$ is lower alkyl and $R_3$ is CN, then $R_1X_2$ is not $C_1$–$C_3$ alkoxy and X is not halogen, methoxy, ethoxy, methylthio, or ethylthio;

or the pharmaceutically acceptable salts thereof.

DETAILED DESCRIPTION OF THE INVENTION

This invention also relates to a method of mediating or inhibiting the enzymatic activity (or catalytic activity) of PDE IV in a mammal in need thereof and to inhibiting the production of TNF in a mammal in need thereof, which comprises administering to said mammal an effective amount of a compound of Formula (I) or (II).

Phosphodiesterase IV inhibitors are useful in the treatment of a variety of allergic and inflammatory diseases including: asthma, chronic bronchitis, atopic dermatitis, urticaria, allergic rhinitis, allergic conjunctivitis, vernal conjunctivitis, eosinophilic granuloma, psoriasis, rheumatoid arthritis, septic shock, ulcerative colitis, Crohn's disease, reperfusion injury of the myocardium and brain, chronic glomerulonephritis, endotoxic shock and adult respiratory distress syndrome. In addition, PDE IV inhibitors are useful in the treatment of diabetes insipidus and central nervous system disorders such as depression and multi-infarct dementia.

The viruses contemplated for treatment herein are those that produce TNF as a result of infection, or those which are sensitive to inhibition, such as by decreased replication, directly or indirectly, by the TNF inhibitors of Formula (I) or (II). Such viruses include, but are not limited to HIV-1, HIV-2 and HIV-3, cytomegalovirus (CMV), influenza, adenovirus and the Herpes group of viruses, such as, but not limited to, Herpes zoster and Herpes simplex.

This invention more specifically relates to a method of treating a mammal, afflicted with a human immunodeficiency virus (HIV), which comprises administering to such mammal an effective TNF inhibiting amount of a compound of Formula (I) or (II).

The compounds of this invention may also be used in association with the veterinary treatment of animals, other than in humans, in need of inhibition of TNF production. TNF mediated diseases for treatment, therapeutically or prophylactically, in animals include disease states such as those noted above, but in particular viral infections. Examples of such viruses include, but are not limited to feline immunodeficiency virus (FIV) or other retroviral infection such as equine infectious anemia virus, caprine arthritis virus, visna virus, maedi virus and other lentiviruses.

The compounds of this invention are also useful in treating yeast and fungal infections, where such yeast and fungi are sensitive to upregulation by TNF or will elicit TNF production in vivo. A preferred disease state for treatment is fungal meningitis. Additionally, the compounds of Formula (I) or (II) may be administered in conjunction with other drugs of choice for systemic yeast and fungal infections. Drugs of choice for fungal infections, include but are not limited to the class of compounds called the polymixins, such as Polymycin B, the class of compounds called the imidazoles, such as clotrimazole, econazole, miconazole, and ketoconazole; the class of compounds called the triazoles, such as fluconazole, and itranazole, and the class of compound called the Amphotericins, in particular Amphotericin B and liposomal Amphotericin B.

The compounds of Formula (I) or (II) may also be used for inhibiting and/or reducing the toxicity of an and-fungal, anti-bacterial or anti-viral agent by administering an effective amount of a compound of Formula (I) or (II) to a mammal in need of such treatment. Preferably, a compound of Formula (I) or (II) is administered for inhibiting or reducing the toxicity of the Amphotericin class of compounds, in particular Amphotericin B.

Preferred compounds are as follows:

When $R_1$ for the compounds of Formula (I) or (II) is an alkyl substituted by 1 or more halogens, the halogens are preferably fluorine and chlorine, more preferably a $C_{1-4}$ alkyl substituted by 1 or more fluorines. The preferred halo-substituted alkyl chain length is one or two carbons, and most preferred are the moieties —$CF_3$, —$CH_2F$, —$CHF_2$, —$CF2CHF_2$, —$CH_2CF_3$, and —$CH_2CHF_2$. Preferred $R_1$ substitutents for the compounds of Formula (I) are $CH_2$-cyclopropyl, $CH_2$-$C_{5-6}$ cycloalkyl, $C_{4-6}$ cycloalkyl, $C_{7-11}$ polycycloalkyl, (3- or 4-cyclopentenyl), phenyl, tetrahydrofuran-3-yl, benzyl or $C_{1-2}$ alkyl optionally substituted by 1 or more fluorines, —$(CH_2)_{1-3}C(O)O(CH_2)_{0-2}CH_3$, —$(CH_2)_{1-3}O(CH_2)_{0-2}CH_3$, and —$(CH_2)_{2-4}OH$.

When the $R_1$ term is $(CR_4R_5)$, the $R_4$ and $R_5$ terms are independently hydrogen or alkyl. This allows for branching of the individual methylene units as $(CR_4R_5)_n$ or $(CR_4R_5)_m$; each repeating methylene unit is independent of the other, e.g., $(CR_4R_5)_n$ wherein n is 2 can be —$CH_2CH(—CH_3)$—, for instance. The individual hydrogen atoms of the repeating methylene unit or the branching hydrocarbon can optionally be substituted by fluorine independent of each other to yield, for instance, the preferred $R_1$ substitutions, as noted above.

When $R_1$ is a $C_{7-11}$ polycycloalkyl, examples are bicyclo [2.2.1]-heptyl, bicyclo[2.2.2]octyl, bicyclo[3.2.1]octyl, tricyclo[5.2.1.0$^{2,6}$]decyl, etc. additional examples of which are described in Saccamano et al., WO 87/06576, published 5 Nov. 1987, whose disclosure is incorporated herein by reference in its entirety.

Preferred Z terms are O, NCN, $NR_7$, $NOR_{14}$, $NOR_{15}$, $NNR_4R_{14}$, $NNR_4R_{15}$, dimethyl ketal or dimethylthio ketal. More preferred are O or NOH.

Preferred X groups for Formula (I) are those wherein X is $YR_2$ and Y is oxygen. The preferred $X_2$ group for Formula (I) is that wherein $X_2$ is oxygen. The preferred $X_3$ group for Formula (I) is that wherein $X_3$ is hydrogen. Preferred $R_2$ groups, where applicable, is a $C_{1-2}$ alkyl optionally substituted by 1 or more halogens. The halogen atoms are preferably fluorine and chlorine, more preferably fluorine. More preferred $R_2$ groups are those wherein $R_2$ is methyl, or the fluoro-substituted alkyls, specifically a $C_{1-2}$ alkyl, such as a —$CF_3$, —$CHF_2$, or —$CH_2CHF_2$ moiety. Most preferred are the —$CHF_2$ and —$CH_3$ moieties.

Preferred $R_3$ moieties are C(O)$NH_2$, C≡$CR_8$, CN, C(Z') H, $CH_2OH$, $CH_2F$, $CF_2H$, and $CF_3$. More preferred are C≡CH and CN. Z' is preferably O or $NOR_8$.

Preferred R₇ moieties include optionally substituted —(CH₂)₁₋₂(cyclopropyl), —(CH₂)₀₋₂(cyclobutyl), —(CH₂)₀₋₂ (cyclopentyl), —(CH₂)₀₋₂(cyclohexyl), —(CH₂)₀₋₂(2-, 3- or 4-pyridyl), (CH₂)₁₋₂(2-imidazolyl), (CH₂)₂(4-morpholinyl), (CH₂)₂(4-piperazinyl), (CH₂)₁₋₂(2-thienyl), (CH₂)₁₋₂(4-thiazolyl), and (CH₂)₀₋₂phenyl;

Preferred rings when R₁₀ and R₁₁ in the moiety —NR₁₀R₁₁ together with the nitrogen to which they are attached form a 5 to 7 membered ring optionally containing at least one additional heteroatom selected from O, N, or S include, but are not limited to 1-imidazolyl, 2-(R₈)-1-imidazolyl, 1-pyrazolyl, 3-(R₈)-1-pyrazolyl, 1-triazolyl, 2-triazolyl, 5-(R₈)-1-triazolyl, 5-(R₈)-2-triazolyl, 5-(R₈)-1-tetrazolyl, 5-(R₈)-2-tetrazolyl, 1tetrazolyl, 2-tetrazloyl, morpholinyl, piperazinyl, 4-(R₈)-1-piperazinyl, or pyrrolyl ring.

Preferred rings when R₈ and R₁₄ in the moiety —NR₈R₁₄ together with the nitrogen to which they are attached may form a 5 to 7 membered ring optionally containing at least one additional heteroatom selected from O, N, or S include, but are not limited to 1-imidazolyl, 1-pyrazolyl, 1-triazolyl, 2-triazolyl, 1-tetrazolyl, 2-tetrazolyl, morpholinyl, piperazinyl, and pyrrolyl. The respective rings may be additionally substituted, where applicable, on an available nitrogen or carbon by the moiety R₇ as described herein for Formula (I). Illustrations of such carbon substitutions includes, but is not limited to, 2-(R₇)-1-imidazolyl, 4-(R₇)-1-imidazolyl, 5-(R₇)-1-imidazolyl, 3-(R₇)-1 pyrazolyl, 4-(R₇)-1-pyrazolyl, 5-(R₇)-1-pyrazolyl, 4-(R₇)-2-triazolyl, 5-(R₇)-2-triazol, 4-(R₇)-1-triazolyl, 5-(R₇)-1-triazolyl, 5-(R₇)-1-tetrazolyl, and 5-(R₇)-2tetrazolyl. Applicable nitrogen substitution by R₇ includes, but is not limited to, 1-(R₇)-2-tetrazolyl, 2-(R₇)-1-tetrazolyl, 4-(R₇)-1-piperazinyl. Where applicable, the ring may be substituted one or more times by R₇.

Preferred groups for NR₈R₁₄ which contain a heterocyclic ring are 5-(R₁₄)-1-tetrazolyl, 2-(R₁₄)-1-imidazolyl, 5-(R₁₄)-2-tetrazolyl, 4-(R₁₄)-1-piperazinyl, or 4-(R₁₅)-1-piperazinyl.

Preferred rings for R₁₃ include (2-, 4- or 5-imidazolyl), (3-, 4- or 5-pyrazolyl), (4- or 5-triazolyl[1,2,3]), (3- or 5-triazolyl[1,2,4]), (5-tetrazolyl), (2-, 4- or 5-oxazolyl), (3-, 4- or 5-isoxazolyl), (3- or 5-oxadiazolyl[1,2,4]), (2-oxadiazolyl[1,3,4]), (2-thiadiazolyl[1,3,4]), (2-, 4-, or 5-thiazolyl), (2-, 4-, or 5-oxazolidinyl), (2-, 4-, or 5-thiazolidinyl), or (2-, 4-, or 5-imidazolidinyl).

When the R₇ group is optionally substituted by a heterocyclic ring such as imidazolyl, pyrazolyl, triazolyl, tetrazolyl, or thiazolyl, the heterocyclic ring itself may be optionally substituted by R₈ either on an available nitrogen or carbon atom, such as 1-(R₈)-2-imidazolyl, 1-(R₈)-4-imidazolyl, 1-(R₈)-5-imidazolyl, 1-(R₈)-3-pyrazoly, 1-(R₈)-4pyrazolyl, 1-(R₈)-5-pyrazolyl, 1-(R₈)-4-triazolyl, or 1-(R₈)-5-triazolyl. Where applicable, the ring may be substituted one or more times by R₈.

Preferred are those compounds of Formula (I) wherein R₁ is —CH₂-cyclopropyl, —CH₂-C₅₋₆ cycloalkyl, —C₄₋₆ cycloalkyl, tetrahydrofuran-3-yl, (3- or 4-cyclopentenyl), benzyl or —C₁₋₂ alkyl optionally substituted by 1 or more fluorines, and —(CH₂)₂₋₄ OH; R₂ is methyl or fluoro-substituted alkyl, R₃ is CN or C≡CR₈; and X is YR₂.

Most preferred are those compounds wherein R₁ is —CH₂-cyclopropyl, cyclopentyl, methyl or CF₂H; R₃ is CN or C≡CH; X is YR₂; Y is oxygen; X₂ is oxygen; X₃ is hydrogen; and R₂ is CF₂H or methyl.

A preferred subgenus of Formula (I) are the compounds of Formula (Ia)

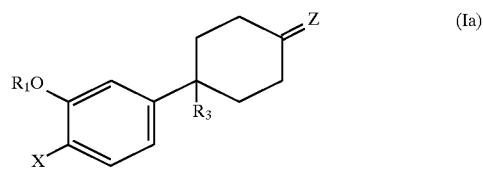

wherein:
R₁ is CH₂-cyclopropyl, CH₂-C₅₋₆ cycloalkyl, C₄₋₆ cycloalkyl, C₇₋₁₁ polycycloalkyl, (3- or 4-cyclopentenyl), phenyl, tetrahydrofuran-3-yl, benzyl or C₁₋₂ alkyl optionally substituted by 1 or more fluorines, —(CH₂)₁₋₃C(O)O(CH₂)₀₋₂CH₃, —(CH₂)₁₋₃O(CH₂)₀₋₂CH₃, and —(CH₂)₂₋₄OH;

X is YR₂, halogen, nitro, NR₄R₅, or formyl amine;

Y is O or S(O)ₘ';

m' is 0, 1, or 2;

R₂ is —CH₃ or —CH₂CH₃ optionally substituted by 1 or more halogens;

R₃ is hydrogen, C₁₋₄ alkyl, halo-substituted C₁₋₄ alkyl CH₂C(O)C(O)N, CH₂NHC(O)C(O)NH₂, CN, CH₂OR₈, C(Z')H, C(O)OR₈, C(O)NR₈R₁₀, or C≡CR₈;

Z' is O or NOR₈;

Z is O, NR₇, NOR₁₄, NOR₁₅, NNR₄R₁₄, NNR₄R₁₅, NCN, or =Z is 2-(1,3-dithiane), dimethylthio ketal, 2-(1,3-dioxolane), or dimethyl ketal;

R₇ is —(CR₄R₅)qR₁₂ or C₁₋₆ alkyl wherein the R₁₂ or C₁₋₆ alkyl group is optionally substituted one or more times by C₁₋₂ alkyl optionally substituted by one to three fluorines, —F, —Br, —Cl, —NO₂, —Si(R₄)₃, —NR₁₀R₁₁, —C(O)R₈, —CO₂R₈, —OR₈, —CN, —C(O)NR₁₀R₁₁, —OC(O)NR₁₀R₁₁, —OC(O)R₈, —NR₁₀C(O)NR₁₀R₁₁, —NR₁₀C(O)R₁₁, —NR₁₀C(O)OR₉, —NR₁₀C(O)R₁₃, —C(NR₁₀)NR₁₀R₁₁, —C(NCN)NR₁₀R₁₁, —C(NCN)SR₉, —NR₁₀C(NCN)SR₉, —NR₁₀C(NCN)NR₁₀R₁₁, —NR₁₀S(O)₂R₉, —S(O)ₘ'R₉, —NR₁₀C(O)C(O)NR₁₀R₁₁, —NR₁₀C(O)C(O)R₁₀, thiazolyl, imidazolyl, oxazolyl, pyrazolyl, triazolyl, or tetrazolyl;

q is 0, 1, or 2;

R₁₂ is C₃₋₇ cycloalkyl, (2-, 3- or 4-pyridyl), (1- or 2-imidazolyl), piperazinyl, morpholinyl, (2- or 3-thienyl), (4- or 5-thiazolyl), or phenyl;

R₈ is independently selected from hydrogen or R₉;

R₉ is C₁₋₄ alkyl optionally substituted by one to three fluorines;

R₁₀ is OR₈ or R₁₁;

R₁₁ is hydrogen or C₁₋₄ alkyl optionally substituted by one to three fluorines; or when R₁₀ and R₁₁ are as NR₁₀R₁₁ they may together with the nitrogen form a 5 to 7 membered ring optionally containing at least one additional heteroatom selected from O, N, or S;

R₁₃ is oxazolidinyl, oxazolyl, thiazolyl, pyrazolyl, triazolyl, tetrazolyl, imidazolyl, imidazolidinyl, thiazolidinyl, isoxazolyl, oxadiazolyl, or thiadiazolyl, and each of these heterocyclic rings is connected through a carbon atom and each may be unsubstituted or substituted by one or two C₁₋₂ alkyl groups;

R₁₄ is hydrogen or R₇; or when R₈ and R₁₄ are as NR₈R₁₄ they may together with the nitrogen form a 5 to 7 membered ring optionally containing one or more additional heteroatoms selected from O, N, or S;

$R_{15}$ is $C(O)R_{14}$, $C(O)NR_4R_{14}$, $S(O)_2R_7$, or $S(O)_2NR_4R_{14}$;

provided that:
a) when Z is O, X is $YR_2$, Y is oxygen, $R_2$ is $CH_3$, and $R_1$ is $CH_3$, then $R_3$ is other than CN;
b) when $R_{12}$ is N-imidazolyl, N-triazolyl, N-pyrrolyl, N-piperazinyl, or N-morpholinyl, then q is not 1;

or the pharmaceutically acceptable salts thereof.

Exemplified preferred compounds of Formula (I) are:
4-cyano-4-(3-cyclopentyloxy-4-methoxyphenyl) cyclohexan-1-one;
4-(3,4-bisdifluoromethoxyphenyl)-4-cyanocyclohexan-1-one;
4-cyano-4-(3-difluoromethoxy-4-methoxyphenyl) cyclohexan-1-one;
4-cyano-4-(3-cyclopropmethoxy-4-methoxyphenyl) cyclohexan-1-one;
4-cyano-4-(3-cyclopentyloxy-4-difluoromethoxyphenyl) cyclohexan-1-one;
4-cyano-4-(3-cyclopropylmethoxy-4-difluoromethoxyphenyl)cyclohexan-1-one;
4-cyano-4-(3-cyclopentyloxy-4-methoxyphenyl) cyclohexan-1-one oxime;
4-(3-cyclopentyloxy-4-methoxyphenyl)-4-formylcyclohexan-1-one;
4-cyano-4-(3-cyclopentyloxy-4-methoxyphenyl) cyclohexan-1-one dimethyl ketal;
4-(3-cyclopentyloxy-4-methoxyphenyl)-4-formylcyclohexan-1-one dimethyl ketal;
4-(3-cyclopentyloxy-4-methoxyphenyl)-4-(hydroxymethyl) cyclohexan-1-one;
4-(3-cyclopentyloxy-4-methoxyphenyl)-4-(hydroxymethyl) cyclohexan-1-one-dimethyl ketal;
4-(3-cyclopentyloxy-4-methoxyphenyl)-4-(fluoromethyl) cyclohexan-1-one;
4-(3-cyclopentyloxy-4-methoxyphenyl)-4-(fluoromethyl) cyclohexan-1-one dimethyl ketal;
4-aminocarbonyl-4-(3-cyclopentyloxy-4-methoxyphenyl) cyclohexan-1-one;
4-aminocarbonyl-4-(3-cyclopentyloxy-4-methoxyphenyl) cyclohexan-1-one dimethyl ketal;
4-(3-cyclopentyloxy-4-methoxyphenyl)-4-ethynylcyclohexan-1-one;
4-(3-cyclopentyloxy-4-methoxyphenyl)-4-ethynylcyclohex-1-one dimethyl ketal;
4-(3,4-bisdifluoromethoxyphenyl)-4-ethynylcyclohexan-1-one;
4-(3,4-bisdifluoromethoxyphenyl)-4-cyanocyclohexan-1-one dimethyl ketal;
4-(3,4-bisdifluoromethoxyphenyl)-4-formylcyclohexan-1-one dimethyl ketal;
4-(3,4-bisdifluoromethoxy)-4-ethynylcyclohex-1-one dimethyl ketal;
4-(3,4-bisdifluoromethoxyphenyl)-4-(oxamidomethyl) cyclohexan-1-one;
4-aminomethyl-4-(3,4-bisdifluoromethoxyphenyl) cyclohexan-1-one dimethyl ketal;
4-(3,4-bisdifluoromethoxyphenyl)-4-(oxamidomethyl) cyclohexan-1-one dimethyl ketal;
4-cyano-4-[3-cyclopentyloxy-4-(4-fluorobenzyloxy) phenyl]cyclohexan-1-one;
4-cyano-4-[3-cyclopentyloxy-4-(4-fluorobenzyloxy) phenyl]cyclohexan-1-one oxime;
4-(3-cyclopropylmethoxy-4-difluoromethoxyphenyl)-4-ethynylcyclohexan-1-one;
4-cyano-4-(3-cyclopropmethoxy-4-methoxyphenyl) cyclohexan-1-one oxime.

Preferred Z" groups are for compounds of the Formula (II) are $C(O)R_{14}$, $C(O)OR_{14}$, $C(O)NR_{10}R_{14}$, $C(NR_{10})NR_{10}R_{14}$, CN, $C(NOR_8)R_{14}$, $C(O)NR_8NR_8C(O)R_8$, $C(O)NR_8NR_{10}R_{14}$, $C(NOR_{14})R_8$, $C(NR_8)NR_{10}R_{14}$, $C(NR_{14})NR_8R_8$, $C(NCN)NR_{10}R_{14}$, $C(NCN)SR_9$, (1-, 4- or 5-$\{R_{14}\}$-2-imidazolyl), (1-, 4- or 5-$\{R_{14}\}$-3-pyrazolyl), (1-, 2- or 5-$\{R_{14}\}$-4-triazoly[1,2,3]), (1-, 2-, 4- or 5-$\{R_{14}\}$-3-triazolyl [1,2,4]), (1- or 2- $\{R_{14}\}$-5-tetrazolyl), (4- or 5-$\{R_{14}\}$-2-oxazolyl), (3- or 4-$\{R_{14}\}$-5-isoxazolyl), (3-$\{R_{14}\}$-5-oxadiazolyl[1,2,4]), (5-$\{R_{14}\}$-3-oxadiazolyl[1,2,4]), (5-$\{R_{14}\}$-2-oxadiazolyl[1,3,4]), (5-$\{R_{14}\}$-2-thiadiazolyl[1,3,4]), (4- or 5-$\{R_{14}\}$-2-thiazolyl), (4- or 5-$\{R_{14}\}$-2-oxazolidinyl), (4- or 5-$\{R_{14}\}$-2-thiazolidinyl),(1-, 4- or 5-$\{R_{14}\}$-2-imidazolidinyl). The remaining preferred substituents for compounds of the Formula (II) are the same as those listed above for compounds of the Formula (I), where applicable.

Exemplified preferred compounds of Formula (II) are:
2-carbomethoxy-4-cyano-4-(3-cyclopentyloxy-4-methoxyphenyl)cyclohexan-1-one;
4-(3,4-bisdifluoromethoxyphenyl)-2-carbomethoxy-4-cyanocyclohexan-1-one;
2-carbomethoxy-4-cyano-4-(3-difluoromethoxy-4-methoxyphenyl)cyclohexan-1-one;
2-carbomethoxy-4-cyano-4-(3-cyclopropylmethoxy-4-methoxyphenyl)cyclohexan-1-one;
2-carbomethoxy-4-cyano-4-(3-cyclopentyloxy-4-difluoromethoxyphenyl)cyclohexan-1-one;
2-carbomethoxy-4-cyano-4-(3-cyclopropylmethoxy-4-difluoromethoxyphenyl)-cyclohexan-1-one;
2-aminocarbonyl-4-cyano-4-(3-cyclopropylmethoxy-4-methoxyphenyl)cyclohexan-1-one;
4-cyano-4-(3-cyclopropylmethoxy-4-difluoromethoxyphenyl)-2-[2-(trimethylsilyl)-ethoxycarbonyl)]-cyclohexan-1-one;
2-carboxy-4-cyano-4-(3-cyclopropylmethoxy-4-difluoromethoxyphenyl)cyclohexan-1-one;
4-(3-cyclopropylmethoxy-4-difluoromethoxyphenyl)-2,4-dicyanocyclohexan-1-one; and
2-aminocarbonyl-4-cyano-4-(3-cyclopropylmethoxy-4-difluoromethoxyphenyl)cyclohexan-1-one.

It will be recognized that some of the compounds of Formula (I) and (II) may exist in both racemic and optically active forms; some may also exist in distinct diastereomeric forms possessing distinct physical and biological properties. All of these compounds are considered to be within the scope of the present invention.

Some compounds of Formula (I) or (II) may exist in a tautomeric form, such as the enol. This may be represented by the ═O being exocyclic to the cyclohexane ring (or

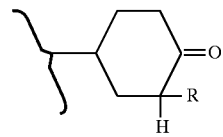

) as contrasted to the endocyclic or —C(—OH)═C(R)— moiety wherein the cyclohexane ring is now unsaturated in the 1–2 position, i.e. cyclohex-1-ene, or

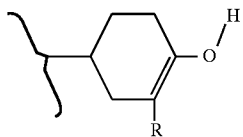

and R is H in Formula (I) or Z" in Formula (II). It is also recognized that the 2-position of the ring in the endocyclic form can be substituted (R) such as in the compounds of Formula (II).

The term "$C_{1-3}$ alkyl", "$C_{1-4}$ alkyl", "$C_{1-6}$ alkyl" or "alkyl" groups as used herein is meant to include both straight or branched chain radicals of 1 to 10, unless the chain length is limited thereto, including, but not limited to methyl, ethyl, n-propyl, isopropyl, n-butyl, sec-butyl, isobutyl, tert-butyl, and the like.

"Alkenyl" means both straight or branched chain radicals of 1 to 6 carbon lengths, unless the chain length is limited thereto, including but not limited to vinyl, 1-propenyl, 2-propenyl, 2-propynyl, or 3-methyl-2-propenyl.

The term "cycloalkyl" or "cycloalkyl alkyl" means groups of 3–7 carbon atoms, such as cyclopropyl, cyclopropylmethyl, cyclopentyl, or cyclohexyl.

"Aryl" or "aralkyl", unless specified otherwise, means an aromatic ring or ring system of 6–10 carbon atoms, such as phenyl, benzyl, phenethyl, or naphthyl. Preferably the aryl is monocyclic, i.e, phenyl. The alkyl chain is meant to include both straight or branched chain radicals of 1 to 4 carbon atoms.

"Heteroaryl" means an aromatic ring system containing one or more heteroatoms, such as imidazolyl, triazolyl, oxazolyl, pyridyl, pyrimidyl, pyrazolyl, pyrrolyl, furanyl, or thienyl.

"Halo" means all halogens, i.e., chloro, fluoro, bromo, or iodo.

"Inhibiting the production of IL-1" or "inhibiting the production of TNF" means:

a) a decrease of excessive in vivo IL-1 or TNF levels, respectively, in a human to normal levels or below normal levels by inhibition of the in vivo release of IL-1 by all cells, including but not limited to monocytes or macrophages;

b) a down regulation, at the translational or transcriptional level, of excessive in vivo IL-1 or TNF levels, respectively, in a human to normal levels or below normal levels; or c) a down regulation, by inhibition of the direct synthesis of IL-1 or TNF levels as a postransational event.

The phrase "TNF mediated disease or disease states" means any and all disease states in which TNF plays a role, either by production of TNF itself, or by TNF causing another cytokine to be released, such as but not limited to IL-1 or IL-6. A disease state in which IL-1, for instance is a major component, and whose production or action, is exacerbated or secreted in response to TNF, would therefore be considered a disease state mediated by TNF. As TNF-β (also known as lymphotoxin) has close structural homology with TNF-α (also known as cachectin), and since each induces similar biologic responses and binds to the same cellular receptor, both TNF-α and TNF-β are inhibited by the compounds of the present invention and thus are herein referred to collectively as "TNF" unless specifically delineated otherwise. Preferably TNF-α is inhibited.

"Cytokine" means any secreted polypeptide that affects the functions of cells, and is a molecule which modulates interactions between cells in immune, inflammatory, or hematopoietic responses. A cytokine includes, but is not limited to, monokines and lymphokines regardless of which cells produce them.

The cytokine inhibited by the present invention for use in the treatment of a HIV-infected human must be a cytokine which is implicated in (a) the initiation and/or maintenance of T cell activation and/or activated T cell-mediated HIV gene expression and/or replication, and/or (b) any cytokine-mediated disease associated problem such as cachexia or muscle degeneration. Preferably, his cytokine is TNF-α.

All of the compounds of Formula (I) and (II) are useful in the method of inhibiting the production of TNF, preferably by macrophages, monocytes or macrophages and monocytes, in a mammal, including humans, in need thereof. All of the compounds of Formula (I) and (II) are useful in the method of inhibiting or mediating the enzymatic or catalytic activity of PDE IV and in treatment of disease states mediated thereby.

Methods of Preparation

Preparing compounds of Formula (I) can be carried out by one of skill in the art according to the procedures outlined in the Examples, infra. The preparation of any remaining compounds of Formula (I) not described therein may be prepared by the analogous processes disclosed herein which comprise:

a) for compounds wherein X and $X_1$ are other than Br, I, $NO_2$, amine, formyl amine, or S(O)m' when m' is 1 or 2, reacting a compound of Formula (2)

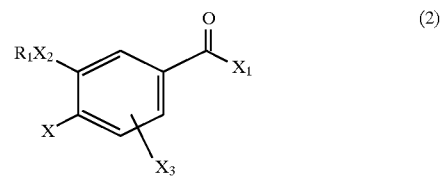

wherein $R_1$ represents $R_1$ as defined in relation to Formula (I) or a group convertable to $R_1$ and X represents X as defined in relation to Formula (I) or a group convertable to X and $X_3$ represents $X_3$ as defined in relation to Formula (I) or a group convertable to $X_3$ and $X_1$ is H, with a lithium halide and a silyl halide in an appropriate solvent followed by reduction with an appropriate reductant, such as a siloxane, to provide a compound of Formula (3) wherein $X_4$ is a halide. Alternatively, reduction of a compound of Formula (2) wherein $X_1$ is H with a suitable reductant, such as sodium borohydride, provides a compound of Formula (3) wherein $X_4$ is OH. Reaction of such a compound of Formula (3) with, for example, phosphorous trichloride, thionyl chloride, phosphorous tribromide, cupric bromide, or carbon tetrabromide and triphenylphosphine, also provides a compound of Formula (3) wherein $X_4$ is a halide;

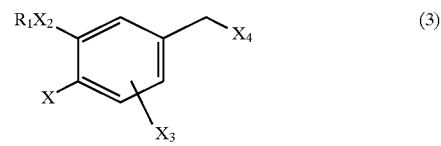

halide displacement by cyanide provides a compound of Formula (3) wherein $X_4$ is CN. Reaction of a compound of Formula (3) wherein $X_4$ is CN with an excess of an acrylate, such as methyl, ethyl, phenyl, benzyl or t-butyl acrylate, in the presence of a base, such as excess metal hydride or catalytic or excess quaternary amine base, such as benzyltrimethylammonium hydroxide, in a suitable non-reacting solvent, such as tetrahydrofuran or 1,2-dimethoxyethane when a metal hydride base is used or these solvents or acetonitrile when a quaternary amine base is used, then provides a compound of Formula (4) in which $X_4$ is CN and $R_{16}$ is an alkyl, phenyl, or benzyl group;

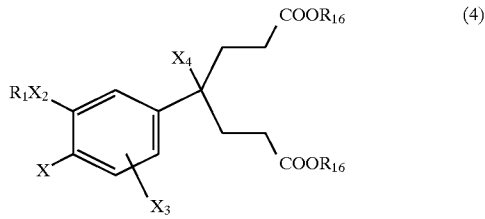

(4)

reaction of a compound of Formula (4) with a base, such as excess metal hydride, in a suitable non-reacting solvent, such as tetrahydrofuran or 1,2dimethoxyethane, at an elevated temperature then provides a compound of Formula (5) wherein $X_4$ is CN and $R_{16}$ is an alkyl, phenyl, or benzyl group;

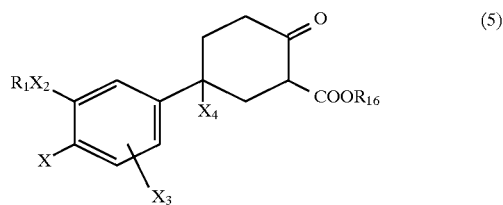

(5)

alternatively, a compound of Formula (5) [a subset of the compounds of Formula (II)] may be obtained directly from a compound of Formula (3) wherein $X_4$ and $R_{16}$ are as described above by reaction with an excess of an acrylate, such as methyl, ethyl, phenyl, benzyl, or t-butyl acrylate, with excess base, such as a metal hydride, in a suitable non-reacting solvent, such as tetrahydrofuran or 1,2-dimethoxyethane, at an elevated temperature.

Treating a compound of Formula (5) with, e.g., sodium chloride in aqueous dimethylsulfoxide at elevated temperature, effects saponification and decarboxylation of the ester moiety to provide a compound of Formula (I) in which $R_3$ is CN and Z is O. Alternatively, a compound of Formula (2) wherein $X_1$ is H may be homologated to a compound of Formula (3) wherein $X_4$ is $COOR_{17}$ by any number of processes known in the art, such as reaction with methyl methylsulfinyl-methyl sulfide and a base, such as sodium hydroxide, followed by treatment with, for example, alcoholic ($R_{17}OH$) acid. Reaction of such a compound of Formula (3) wherein $X_4$ is $COOR_{17}$ with an excess of an acrylate, such as methyl, ethyl, phenyl, benzyl, or t-butyl acrylate, and with excess base, such as a metal hydride, in a suitable non-reacting solvent, such as tetrahydrofuran or 1,2-dimethoxyethane, provides a compound of Formula (4) wherein $X_4$ is $COOR_{17}$ and $R_{16}$ and $R_{17}$ are independently an alkyl, phenyl, or benzyl group. Reaction of a compound of Formula (4) wherein $X_4$ is $COOR_{17}$ and $R_{16}$ and $R_{17}$ are independently an alkyl, phenyl, or benzyl group with a base, such as excess metal hydride, in a suitable non-reacting solvent, such as tetrahydrofuran or 1,2-dimethoxyethane, at an elevated temperature then provides a compound of Formula (5) wherein $X_1$ is $COOR_{17}$ and $R_{16}$ and $R_{17}$ are independently an alkyl, phenyl or benzyl group. Treatment of a such a compound of Formula (5) with, e.g., sodium chloride in aqueous dimethylsulfoxide at elevated temperature effects saponification and decarboxylation of the β-keto ester moiety to provide a compound of Formula (I) wherein $R_3$ is $COOR_{17}$ and Z is O, although under certain reaction conditions, some compounds of Formula (I) wherein $R_3$ is COOH and Z is O will also be obtained. The carboxyl group of such a compound of Formula (I) may then be converted into a number of esters, in which $R_3$ is $COOR_8$, or amides, in which $R_3$ is $CONR_8R_8$, using any of the very wide varieties of standard transformations known in the art. In some cases, the keto carbonyl of such a compound of Formula (I) may require protection as, e.g., a ketal, prior to ester or amide formation, with liberation of the protected ketone under appropriate mild acidic conditions as the final step. The simple amide derivative, that in which $R_3$ is $CONH_2$ and Z is O, may be treated, after appropriate protection of the ketone, with a dehydrating agent to provide, after ketone deprotection, the compound of Formula (I) in which $R_3$ is CN and Z is O.

Compounds of Formula (I) wherein $R_3$ is CHO and Z is O may be prepared from the compound of Formula (I) in which $R_3$ is CN and Z is O after appropriate protection of the ketone as, e.g., a ketal, followed by reduction of the CN moiety with, e.g., di-isobutylaluminum hydride, followed by appropriate workup and ketone deprotection.

Compounds of Formula (I) wherein $R_3$ is $CH_2OH$ and Z is O may be prepared by reduction of the compound of Formula (I) in which $R_3$ is CHO and =Z is a ketal protecting group with, e.g., sodium borohydride, followed by appropriate workup and ketone deprotection.

Compounds of Formula (I) wherein $R_3$ is $CH_2NR_8R_8$ and Z is O may be prepared by reduction of the compound of Formula (I) in which $R_3$ is CN and =Z is a ketal protecting group with, e.g., lithium aluminum hydride or hydrogen in the presence of a catalyst, followed by appropriate workup, standard alkylation by $R_8$ and then ketone deprotection.

Compounds of Formula (I) wherein $R_3$ is OH and Z is O may be prepared from the compound of Formula (I) in which $R_3$ is CHO and =Z is a ketal protecting group by, e.g., Bayer-Villiger oxidation of the aldehyde and ester saponification to provide the compound of Formula (I) in which $R_3$ is OH and =Z is a ketal protecting group, followed by ketone deprotection.

Compounds of Formula (I) wherein $R_3$ is halogen and Z is O may be prepared from the compound of Formula (I) in which $R_3$ is OH and =Z is a ketal protecting group by, e.g., dehydration to the olefin and hydrohalic acid addition to provide the compound of Formula (I) in which $R_3$ is halogen and =Z is a ketal protecting group, followed by ketone deprotection.

Compounds of Formula (I) wherein $R_3$ is $C\equiv CR_{8'}$ and Z is O may be prepared from the compound of Formula (I) in which $R_3$ is CHO and =Z is a ketal protecting group by reaction with a mixture of dimethyl (diazomethyl) phosphonate and potassium t-butoxide or other suitable base, in an inert solvent, such as tetrahydrofuran, at reduced temperature, followed by appropriate workup and ketone deprotection to provide the compounds of Formula (I) wherein $R_3$ is $C\equiv CH$; alternatively, prior to ketone deprotection, alkylation of the acetylene under the appropriate conditions with a strong base followed by an alkylating agent, $R_8L$, wherein L is a leaving group and $R_{8'}$ is not H, followed by ketone deprotection, provides compounds of Formula (I) wherein $R_3$ is $C\equiv CR_{8'}$, Compounds of Formula (I) wherein $R_3$ is $CH_2F$ and Z is O may be prepared from the compound of Formula (I) wherein $R_3$ is $CH_2OH$ and =Z is a ketal protecting group by treatment with diethyl-aminosulfur trifluoride (DAST) followed by ketone deprotection.

Compounds of Formula (I) wherein $R_3$ is $CHF_2$ and Z is O may be prepared from the compound of Formula (I)

wherein $R_3$ is CHO and =Z is a ketal protecting group by treatment with diethylaminosulfur trifluoride (DAST) followed by ketone deprotection.

Compounds of Formula (I) wherein $R_3$ is $CF_3$ and Z is O may be prepared from the compound of Formula (3) wherein $X_2$ is $CF_3$ using the procedures described above for preparation of the compounds of Formula (I) wherein $R_3$ is CN or $COOR_{16}$ and Z is O; the compound of Formula (3) wherein $X_2$ is $CF_3$ may be prepared in turn from the compound of Formula (2) wherein $X_1$ is H either electrochemically by the method of Shono et al., J. Org. Chem., 56:2–4, 1991, or by treating a compound of Formula (6)

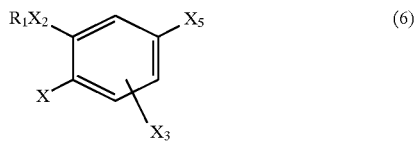

(6)

wherein $X_5$ is, e.g., bromine, with a metalling agent, such as an alkyl lithium, in an inert solvent, such as tetrahydrofuran or 1,2-dimethoxyethane, at −78° C. followed by the trifluoroacetic acid or difluoro acetic acid by the method of Nad et al., Izvest, 71, 1959: Chem. Abstr., 53, No. 14977 and 53, No. 17933, 1959, to provide a compound of Formula (2) wherein $X_1$ is $CF_3$, which is then thioketalized with, e.g., 1,3-propanedithiol and subsequently subjected to desulfurization with, e.g., Raney nickel.

The compounds of Formula (I) where $R_3$ is $C_1$ alkyl and Z is O may be prepared from the compound of Formula (I) wherein $R_3$ is $CH_2OH$ and =Z is a protected ketone by reductive removal of the alcohol with lithium in ammonia, with aluminum hydride, or by conversion of the alcohol to the corresponding thiocarbamate followed by reduction with, e.g., tributyltin hydride or trialkylsilyl hydride, and ketone deprotection; alternatively, the compounds of Formula (I) wherein $R_3$ is $C_1$ alkyl and Z is O may be prepared from the compound of Formula (I) wherein $R_3$ is CHO and =Z is a protected ketone by thioketal formation, desulfurization and ketal deprotection.

Compounds of Formula (I) where $R_3$ is $C_{2-4}$ alkyl or halogen substituted $C_{2-4}$ alkyl and Z is O may be prepared by analogous deoxygenation procedures from the corresponding alcohol derived from reaction of the compound of Formula (I) wherein $R_3$ is CHO and =Z is a protected ketone with a metal alkyl or a halogen substituted $C_{2-4}$ metal alkyl reagent and subsequent deprotection to liberate the =Z ketone.

Compounds of Formula (I) wherein $R_3$ is vinyl and Z is O may be prepared by, e.g., Wittig or other olefination reaction of the compound of Formula (I) wherein $R_3$ is CHO and =Z is a protected ketone, and subsequent deprotection to liberate the =Z ketone.

Compounds of Formula (I) wherein $R_3$ is cyclopropyl and Z is O may be prepared from the compound of Formula (I) wherein $R_3$ is vinyl and =Z is a protected ketone by reaction with, e.g., methylene iodide and zinc-copper couple, with subsequent deprotection to liberate the =Z ketone.

Alternatively, certain compounds of Formula (I) wherein Z is O and $R_3$ is $COOR_8$ (or $COOR_{16}$) may be prepared by reducing the double bond of the cyclohexenone synthetic intermediates produced by the method of Parkinson and Pinhey, J. Chem. Soc. Perkin Trans. I, 1053–7, 1991, incorporated herein by reference in its entirety. Similar double bond reduction of the corresponding synthetic intermediates wherein $R_3$ is CN derived by analogous procedures using 4-cyano-3-cyclohexen-1-one and/or 4-cyano-2-cyclohexen-1-one may provide certain compounds of Formula (I) wherein Z is O and $R_3$ is CN.

Most compounds of Formula (I) wherein Z is not O are prepared from the corresponding compounds of Formula (I) wherein Z is O by reaction with the appropriate amine, alcohol, or thiol, in the presence of a catalyst or with removal of water, if required, as described in the procedures outlined in the Examples, infra; however, when $R_3$ is CHO, this $R_3$ group may require protection as, e.g., a ketal, during reaction followed by deprotection.

b) Compounds of Formula (I) wherein X or $X_3$ is formyl amine and Z is O may be prepared by formylating, at the last step, a compound wherein =Z is a protected ketone and X is $NH_2$, obtained by removal of a protecting group from the amine functionality; such protective groups are well known to those skilled in the art, See Greene, T. and Wuts, P.G.M., Protecting Groups in Organic Synthesis, 2nd Ed., John Wiley and Sons, New York (1991).

c) Compounds of Formula (I) wherein X or $X_3$ is Br or I and Z is O may be prepared from a similarly deprotected amine by diazotization of the amine and diazonium displacement via Sandmeyer reaction.

d) Compounds of Formula (I) wherein X or $X_3$ is $NO_2$ and Z is O may be prepared from a similarly deprotected amine by oxidation of the amine to the nitro group.

e) Compounds of Formula (I) wherein Y is S(O)m' when m' is 1 or 2 and Z is O may be prepared from the compounds of Formula (I) wherein Y is S by oxidation of the $SR_2$ moiety under conditions well known to those skilled in the art.

Compounds of Formula (I) wherein $R_{14}$ in $C(O)OR_{14}$ of the Z" group is other than an alkyl, phenyl, or benzyl group are obtained from compounds of Formula (5) or from other compounds of Formula (II) by standard transesterification procedures. Similarly, other compounds of the Formula (II), e.g., Z" amides, aldehydes, ketones, hydrazides, etc., may be prepared from other compounds of the Formula (II) by, e.g., standard functional group manipulation of the Z" group, either preceeding or following functional group manipulation of the $R_3$ group. In some cases, appropriate protection of certain chemically sensitive $R_3$ groups and/or the keto (=O) moiety of the Formula (II) compound may be required during functional group manipulation of the Z" group, with subsequent deprotection providing the desired Formula (II) compound. Some such manipulations of the Z" group may be accomplished by the processes described in co-pending U.S. application Ser. No. 862,030 filed 2 Apr. 1992 and its corresponding continuation-in-part application U.S. Ser. No. 968,762 filed 30 Oct. 1992. In other cases, some compounds of Formula (II) may be converted to other compounds of Formula (II) by manipulation of the $R_3$ group using the general techniques described above and, when necessary, using appropriate protection and deprotection of chemically sensitive functionalities, such as the keto (=O) moiety or chemically sensitive moieties of the Z" group. Also, some compounds of Formula (II) may be prepared by reaction of an appropriate compound of Formula (I) with an appropriate base in the appropriate proportions under the appropriate conditions followed by reaction with a haloformate, such as methyl or ethyl chloroformate, or by treatment of an appropriate compound of Formula (I) with methyl methoxy magnesium carbonate; such compounds of the Formula (II) may then be converted to other compounds of the Formula (II) by the techniques described above and below.

In addition, some compounds of the Formula (II) may be prepared by reacting a compound of the Formula (3) wherein $R_1$ represents $R_1$ as defined in relation to Formula (I) or a group convertable to $R_1$ and X, $X_2$ and $X_3$ represent X, $X_2$ and $X_3$ as defined in relation to Formula (I) or a group conversable to X, $X_2$ or $X_3$ and $R_3$ represents $R_3$ as defined in relation to Formula (I) or a group convertable to $R_3$, and $X_4$ is CN with an excess of acrylonitrile in the presence of a base, such as excess metal hydride, or catalytic or excess quaternary amine base, such as benzyltrimethylammonium hydroxide, in a suitable non-reacting solvent, such as tetrahydrofuran or 1,2-dimethoxyethane when a metal hydride base is used or these sovents or acetonitrile when a quaternary amine base is used, to provide a compound of the Formula (7)

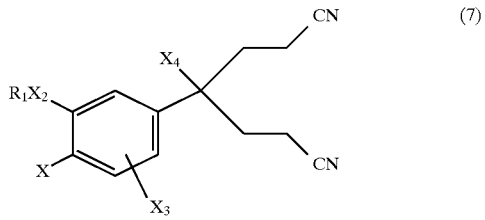

wherein $X_4$ is CN; reaction of a compound of the Formula (7) with a base, such as excess metal hydride, in a suitable non-reacting solvent, such as tetrahydrofuran or 1,2-dimethoxyethane, at an elevated temperature then provides a compound of the Formula (8)

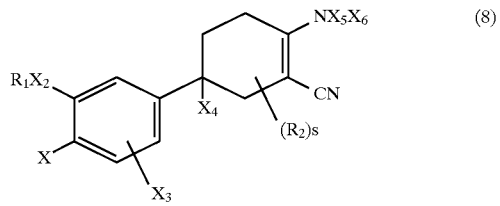

wherein $X_4$ is CN and $X_5$ and $X_6$ are both H; alternatively, a compound of the Formula (8) may be obtained directly from a compound of Formula (7) wherein $X_4$ is as described above by reaction with an excess of optionally $R_2$-substituted acrylonitrile, with excess base, such as a metal hydride, in a suitable non-reacting solvent, such as tetrahydrofuran or 1,2-dimethoxyethane, at an elevated temperature.

Treatment of a compound of the Formula (8) with an acid, e.g., 6N hydrochloric acid at ambient or elevated temperature, in a solvent, such as ethanol, with or without a co-solvent, such as chloroform, provides a compound of Formula (9).

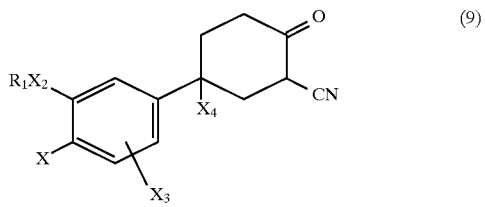

Compounds of the Formula (10)

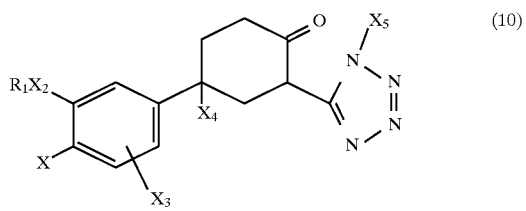

wherein $X_5$ is H, are prepared by heating compounds of the Formula (9) in a solution of hydrazoic acid generated in situ by, e.g., admixture of an alkalai metal azide, such as sodium azide, with an ammonium halide, such as triethylamine hydrochloride, in a polar non-protic solvent such as N-methylpyrrolidinone.

Using the series of reactions outlined above begining with reaction of an appropriate compound of Formula (3) but with a 2-($R_2$)- or 3-($R_2$)-acrylate provides, respectively and sequentially, the 2,6-($R_2$)$_2$- or 3,5-($R_2$)$_2$-pimelates of Formula (4), the 2,6-($R_2$)$_2$- or 3,5-($R_2$)$_2$-2-(COOR$_{16}$)-cyclohexanones of Formula (5) and then the 2,6-($R_2$)$_2$- or 3,5-($R_2$)$_2$-cyclohexanones of Formula (I). Similarly, starting with reaction of an appropriate compound of Formula (3) but with a 2,3-($R_2$)$_2$- or 3,3-($R_2$)$_2$-acrylate provides, respectively and sequentially, the 2,3,5,6-($R_2$)$_4$- or 3,3,5,5-($R_2$)$_4$-pimelates of Formula (4), the 2,3,5,6-($R_2$)$_4$- or 3,3,5,5-($R_2$)$_4$-2-(COOR$_{16}$)-cyclohexanones of Formula (5) and then the 2,3,5,6-($R_2$)$_4$- or 3,3,5,5-($R_2$)$_4$-cyclohexanones of Formula (I). Likewise, starting with reaction of an appropriate compound of Formula (3) but with a mixture of appropriate acrylates, e.g., methyl acrylate and methyl 3-($R_2$)- or 2,3-($R_2$)$_2$-acrylate, provides, respectively and sequentially, e.g., 3-($R_2$)- or 2,3-($R_2$)$_2$-pimelates of Formula (4), the 3-($R_2$)-, 5-($R_2$)-, 5,6($R_2$)$_2$-, or 2,3-($R_2$)$_2$-2-(COOR$_{16}$)-cyclohexanones of Formula (5) and then the 3-($R_2$)- or 2,3-($R_2$)$_2$-($R_2$)$_4$-cyclohexanones of Formula (I). Alternatively, reaction of an appropriate compound of Formula (I) with an appropriate base in the appropriate proportions under the appropriate conditions followed by reaction with an alkylating agent, $R_2L$, wherein L is a leaving group, provides the 2-($R_2$)-, 2,2-($R_2$)$_2$-, 2,6-($R_2$)$_2$-, or 2,2,6,6-($R_2$)$_4$-cyclohexanones of Formula (I); similar reaction of an appropriately alkylated compound of Formula (I), e.g., 3,5-($R_2$)$_2$- or 2,6-($R_2$)$_2$-cyclohexanone, provides, e.g., 2,3,5-($R_2$)$_3$- or 2,2,6-($R_2$)$_3$-cyclohexanone of Formula (I), respectively. Likewise, similar reaction of a compound of Formula (5) provides, e.g., 2-($R_2$)-, 2,6-($R_2$)$_2$-, or 2,6,6-($R_2$)$_3$-2-(COOR$_{16}$)-cyclohexanones of Formula (5); such compounds of Formula (5) may then be converted to the corresponding compounds of Formula (I) by ester saponification and decarboxylation as described above. Such compounds of Formula (I) may then be converted to other compounds of Formula (I) using the general techniques and, when necessary, appropriate protection and deprotection of chemically sensitive functionalities, described above; likewise, such compounds of Formula (II) may be converted to other compounds of Formula (II) using the general techniques and, when necessary, appropriate protection and deprotection of chemically sensitive functionalities, described above.

The following examples are set out to illustrate how to make the compounds of this invention and methods for determining associated therapeutic activity. These examples are not intended to limit the invention in any manner, their purpose is illustrative rather than limiting.

EXAMPLE 1

2-Carbomethoxy-4-cyano-4-(3-cyclopentyloxy-4-methoxyphenyl)-cyclohexan-1-one 1a. (3-Cyclopentyloxy-4-methoxyphenyl)acetonitrile To a solution of 3-cyclopentyloxy-4-methoxybenzaldehyde (20 g, 90.8 mmol) in acetonitrile (100 mL) was added lithium bromide (15 g, 173 mmol) followed by the dropwise addition of trimethylsilychloride (17.4 mL, 137 mmol). After 15 min, the reaction mixture was cooled to 0° C., 1,1,3,3-tetramethyldisiloxane (26.7 mL, 151 mmol) was added dropwise and the resulting mixture was allowed to warm to room temperature. After stirring for 3 h, the mixture was separated into two layers. The lower layer was removed, diluted with methylene chloride and filtered through Celite. The filtrate was concentrated under reduced pressure, dissolved in methylene chloride and refiltered. The solvent was removed in vacuo to provide a light tan oil. To a solution of this crude a-bromo-3-cyclopentyloxy-4-methoxytoluene in dimethylformamide (160 mL) under an argon atmosphere was added sodium cyanide (10.1 g, 206 mmol) and the resulting mixture was stirred at room temperature for 18 h, then poured into cold water (600 mL) and extracted three times with ether. The organic extract was washed three times with water, once with brine and was dried (potassium carbonate). The solvent was removed in vacuo and the residue was purified by flash chromatography, eluting with 10% ethyl acetate/hexanes, to provide an off-white solid (17.7 g, 84%): m.p. 32°–34° C.; an additional quantity (1.3 g) of slightly impure material also was isolated.

1b. Dimethyl 4-cyano-4-(3-cyclopentyloxy-4-methoxyphenyl)pimelate To a solution of (3-cyclopentyloxy-4-methoxyphenyl)acetonitrile (7 g, 30.3 mmol) in acetonitrile (200 mL) under an argon atmosphere was added a 40% solution of Triton-B in methanol (1.4 mL, 3.03 mmol) and the mixture was heated to reflux. Methyl acrylate (27 mL, 303 mmol) was added carefully, the reaction mixture was maintained at reflux for 5 h and then cooled. The mixture was diluted with ether, was washed once with 1N hydrochloric acid and once with brine, was dried (magnesium sulfate) and the solvent was removed in vacuo. The solid residue was triturated with 5% ethanol/hexane to provide a white solid (9 g, 74%): m.p. 81°–82° C.; and additional 1.1 g (9%) was also obtained from the filtrate. Analysis Calc. for $C_{22}H_{29}NO_6$: C 65.49, H 7.25, N 3.47; found: C 65.47, H 7.11, N 3.49.

1c. 2-Carbomethoxy-4-cyano-4-(3-cyclopentyloxy-4-methoxyphenyl)cyclohexan-1-one To a solution of dimethyl 4-cyano-4-(3-cyclopentyloxy-4-methoxyphenyl)pimelate (5.9 g, 14.6 mmol) in dry 1,2-dimethoxyethane (120 mL) under an argon atmosphere was added sodium hydride (80% suspension in mineral oil, 1.05 g, 43.8 mmol). The mixture was heated to reflux for 4.5 h, then was cooled to room temperature and was stirred for 16 h. Water was added and the reaction mixture was partitioned between ether and acidic water. The organic extract was dried (magnesium sulfate) and the solvent was removed in vacuo. The residue was purified by flash chromatography, eluting with 3:1 hexanes/ethyl acetate, to provide a white foam (4.9 g, 93%).

Analysis Calc. for $C_{19}H_{23}NO_3 \cdot \frac{1}{4}H_2O$: C 67.09, H 6.84, N 3.72; found: C 66.92, H 6.61, N 3.74.

EXAMPLE 2

4-(3,4-Bisdifluoromethoxyphenyl)-2-carbomethoxy-4-cyanocyclohexan-1-one 2a. 3,4-Bisdifluoromethoxybenzaldehyde A vigorously stirred mixture of 3,4-dihydroxybenzaldehyde (40 g, 290 mmol) and powdered potassium carbonate (120 g, 870 mol) in dimethylformamide (500 mL) was heated under an atmosphere of chlorodifluoromethane at 80° C. for 7 h and then was stirred at room temperature overnight. The mixture was diluted with ether and was filtered. The filtrate was concentrated under reduced pressure, the residue was partitioned between ether and aqueous potassium carbonate and was extracted five times with ether. The organic extract was washed with aqueous potassium carbonate and dried (potassium carbonate). The solvent was removed in vacuo and the residue was purified by flash chromatography, eluting with 4:1 hexanes/ether, to provide an oil (26.2 g, 38%).

2b. 3,4-Bisdifluoromethoxybenzyl alcohol 3,4-Bisdifluoromethoxybenzaldehyde (26.2 g, 110 mmol) in absolute ethanol (150 mL) was treated with sodium borohydride (8.32 g, 220 mmol) under an argon atmosphere at room temperature for 0.5 h. Ten percent aqueous sodium hydroxide (130 mL) was added, the ethanol was removed in vacuo, the mixture was partitioned between ether and water and was extracted twice with ether. The organic extract was dried (magnesium sulfate) and evaporated to a pale yellow oil (26.4 g, 100%).

2c. 2-(3,4-Bisdifluoromethoxyphenyl)acetonitrile A solution of 3,4-bisdifluoromethoxybenzyl alcohol (26.4 g, 110 mmol) and pyridine (9.79 mL, 120 mmol) in chloroform (200 mL) under an argon atmosphere was treated with thionyl chloride (9.62 mL, 130 mmol) and the mixture was heated at reflux for 1 h. The solvent was removed, ether was added and the precipitate was removed by filtration. The filtrate was concentrated to a purple oil. To a solution of this 3,4-bisdifluoromethoxybenzyl chloride in dimethylformamide (200 mL) under an argon atmosphere was added sodium cyanide (11.86 g, 240 mmol). The resulting mixture was stirred and gently heated at 45° C. for 3 h, was cooled and was concentrated. The mixture was partitioned between ether and 5% aqueous sodium carbonate and was extracted five times with ether. The organic extract was washed once with brine, was dried (sodium carbonate) and the solvent was removed in vacuo to provide an oil (27 g).

2d. Dimethyl 4-cyano-4-(3,4-bisdifluoromethoxyphenyl)-4-cyanopimelate To a solution of 2-(3,4-bisdifluoromethoxyphenyl)acetonitrile (27 g, 108 mmol) and a 40% solution of Triton-B in methanol (5 mL, 11 mmol) in acetonitrile (450 mL) under an argon atmosphere at room temperature was added methyl acrylate (48.6 mL, 540 mmol). After 20 min, aqueous hydrochloric acid (3N, 20 mL) was added and the mixture was concentrated. The residue was partitioned between water and ether, was extracted twice with ether, the ether layer was dried (magnesium sulfate) and evaporated in vacuo to provide a yellow oil (45.32 g, 99%).

2e. 4-(3,4-Bisdifluoromethoxyphenyl)-2-carbomethoxy-4-cyanocyclohexan-1-one To a solution of dimethyl 4-(3,4-bisdifluoromethoxyphenyl)-4-cyanopimelate (45.32 g, 107 mmol) in dry 1,2-dimethoxyethane (450 mL) under an argon atmosphere was added sodium hydride (80% dispersion in mineral oil, 13 g, 432 mmol). The resulting mixture was refluxed for 1 h, was cooled to room temperature, was quenched with water and was concentrated. The mixture was partitioned between ether and acidic brine, was extracted twice with ether, the organic layer was dried (magnesium sulfate) and the solvent was removed in vacuo. The residue was purified by flash chromatography, eluting with 3:1 hexanes/ethyl acetate, to provide a pale-orange oil (19.5 g, 46.6%).

Analysis Calc. for $C_{17}H_{15}F_4NO_5$: C 52.45, H 3.88, N 3.60; found: C 52.60, H 4.07, N 3.22.

EXAMPLE 3

2-Carbomethoxy-4-cyano-4-(3-difluoromethoxy-4-methoxyphenyl)cyclohexan-1-one 3a. 3-Difluoromethoxy-4-methoxybenzaldehyde A vigorously stirred mixture of 3-hydroxy-4-methoxybenzaldehyde (2.5 g, 16.4 mmol) and powdered cesium carbonate (5.6 g, 17.2 mol) in dimethylformamide (50 mL) was heated under an atmosphere of chlorodifluoromethane at 80° C. for 4 h. The mixture was allowed to cool, was poured into water and was extracted three times with ethyl acetate. The organic extract was dried (sodium sulfate) and the solvent was removed in vacuo. Purification by flash chromatography, eluting with 5% ethyl acetate/chloroform, provided an oil (2 g, 60%).

3b. (3-Difluoromethoxy-4-methoxyphenyl)acetonitrile To 3-difluoromethoxy-4-methoxybenzaldehyde (2 g, 9.8 mmol) was added lithium bromide (1.7 g, 19.6 mmol) and acetonitrile (11 mL). Upon dissolution, the reaction mixture was cooled to 0° C. Trimethylsilylchloride (1.86 mL, 14.7 mmol) was slowly added and the reaction mixture was allowed to warm to room temperature and was stirred for 15 min. The reaction mixture was again cooled to 0° C., 1,1,3,3-tetramethyldisiloxane (2.6 mL, 14.7 mmol) was added and the resulting mixture was allowed to warm to room temperature. After stirring for 3 h, the mixture was separated into two layers. The lower layer was removed, diluted with methylene chloride and filtered. The filtrate was concentrated under reduced pressure, dissolved in methylene chloride and refiltered. The solvent was removed in vacuo to provide an oil, which was dissolved in dimethylformamide (10 mL) under an argon atmosphere and treated with sodium cyanide (1.08 g, 22 mmol). The resulting mixture was stirred at room temperature overnight, then poured into cold water (250 mL) and extracted three times with ethyl acetate. The organic extract was washed three times with water, once with brine and was dried (potassium carbonate). The solvent was removed in vacuo to provide a yellow oil (1.54 g, 74%), which was used without purification.

3c. Dimethyl 4-cyano-4-(3-difluoromethoxy-4-methoxyphenyl)pimelate To a solution of (3-difluoromethoxy-4-methoxyphenyl)acetonitrile (1.54 g, 7.2 mmol) in acetonitrile (78 mL) under an argon atmosphere was added a 40% solution of Triton-B in methanol (0.33 mL, 0.72 mmol). The resulting mixture was heated to reflux and methyl acrylate (13 mL, 144 mmol) was added cautiously. After 3 h, the reaction was cooled to room temperature, water was added and the mixture was concentrated. The residue was partitioned between aqueous hydrochloric acid and ethyl acetate, was extracted twice with ethyl acetate, the organic layer was dried (magnesium sulfate) and evaporated. Purification by flash chromatography, eluting with 2:1 hexanes/ethyl acetate, provided a foam (1.7 g, 61%).

3d. 2-Carbomethoxy-4-cyano-4-(3-difluoromethoxy-4-methoxyphenyl)cyclohexan-1-one To a suspension of sodium hydride (95%, 0.33 g, 13.2 mmol) in dry 1,2-dimethoxyethane (70 mL) under an argon atmosphere was added a solution of dimethyl 4-cyano-4-(3-difluoromethoxy-4-methoxyphenyl)pimelate (1.7 g, 4.4 mmol) in dry 1,2-dimethoxyethane (70 mL). The resulting mixture was refluxed for 5 h, cooled to room temperature, stirred overnight and quenched with water. The mixture was partitioned between ethyl acetate and acidic water, extracted three times with ethyl acetate, the organic layer was dried (magnesium sulfate) and the solvent was removed in vacuo. Purification by flash chromatography, eluting with 3:1 hexanes/ethyl acetate, provided an oil (0.51 g, 33%, 51% based on recovered starting material).

EXAMPLE 4

2-Carbomethoxy-4-cyano-4-(3-cyclopropylmethoxy-4-methoxyphenyl)cyclohexan-1-one 4a. 3-Cyclopropylmethoxy-4-methoxybenzaldehyde A vigorously stirred mixture of 3-hydroxy-4-methoxybenzaldehyde (20 g, 131 mmol), chloromethylcyclopropane (18.2 mL, 197 mmol) and powdered potassium carbonate (27.3 g, 197 mol) in dimethylformamide (400 mL) was heated under an argon atmosphere at 80° C. for 9 h. The mixture was allowed to cool and was filtered through Celite. The filtrate was concentrated under reduced pressure, the residue was extracted twice with ethyl acetate, the organic extract was washed five times with saturated aqueous sodium carbonate and was dried (sodium sulfate). The solvent was removed in vacuo to provide an off-white solid (21.2 g, 78%): m.p. 67°–69° C.

4b. (3-Cyclopropylmethoxy-4-methoxyphenyl)acetonitrile To 3-cyclopropylmethoxy-4-methoxybenzaldehyde (21.2 g, 103 mmol) was added lithium bromide (17.8 g, 206 mmol) and acetonitrile (110 mL). Upon dissolution, the reaction mixture was cooled to 0° C. Trimethylsilylchloride (19.6 mL, 154 mmol) was slowly added and the reaction mixture was allowed to warm to room temperature and was stirred for 15 min. The reaction mixture was again cooled to 0° C., 1,1,3,3-tetramethyldisiloxane (27.2 mL, 154 mmol) was added and the resulting mixture was allowed to warm to room temperature. After stirring for 2 h, the mixture was separated into two layers. The lower layer was removed, was diluted with methylene chloride, was filtered and the filtrate was concentrated under reduced pressure; this procedure was repeated a total of three times. The resulting light tan oil was dissolved in dimethylformamide (90 mL) under an argon atmosphere and was treated with sodium cyanide (11.3 g, 232 mmol). The resulting mixture was stirred at room temperature for 2 h, then poured into cold water and extracted twice with ethyl acetate. The combined organic extract was washed three times with water, once with brine and was dried (sodium sulfate). The solvent was removed in vacuo to provide an oil (21.4 g, 96%), which was used without purification.

4c. Dimethyl 4-cyano-4-(3-cyclopropylmethoxy-4-methoxyphenyl)pimelate To a solution of (3-cyclopropylmethoxy-4-methoxyphenyl)acetonitrile (21.4 g, 98.6 mmol) in acetonitrile (400 mL) under an argon atmosphere was added a 40% solution of Triton-B in methanol (4.5 mL, 9.9 mmol). The resulting mixture was heated to reflux and methyl acrylate (178 mL, 197 mmol) was added cautiously. After 3 h, the reaction was cooled to room temperature and concentrated. The residue was partitioned between 10% aqueous hydrochloric acid and ethyl acetate, was extracted three times with ethyl acetate, the organic layer was dried (potassium carbonate) and evaporated. Purification by flash chromatography, eluting with 2:1 hexanes/ethyl acetate, provided an oil (27 g, 71%).

4d. 2-Carbomethoxy-4-cyano-4-(3-cyclopropylmethoxy-4-methoxyphenyl)cyclohexan-1-one To a solution of dimethyl 4-cyano-4-(3-cyclopropylmethoxy-4-methoxyphenyl) pimelate (10.4 g, 26.7 mmol) in dry 1,2-dimethoxyethane (500 mL) under an argon atmosphere was added sodium hydride (80% dispersion in mineral oil, 2.5 g, 31.2 mmol). The resulting mixture was refluxed for 4 h, cooled to room temperature and quenched with water. The mixture was partitioned between ethyl acetate and acidic water, extracted three times, the organic layer was dried (magnesium sulfate) and the solvent was removed in vacuo. The product was purified by flash chromatography, eluting with 2:1 hexanes/ethyl acetate, to provide an oil (9 g, 95%).

Analysis Calc. for $C_{20}H_{23}NO_5 \cdot \frac{1}{8}H_2O$: C 66.79, H 6.52, N 3.89; found: C 66.62, H 6.43, N 3.92.

EXAMPLE 5

2-Carbomethoxy-4-cyano-4-(3-cyclopentyloxy-4-difluoromethoxyphenyl)cyclohexan-1-one 5a. 4-Difluoromethoxy-3-hydroxybenzaldehyde A vigorously stirred mixture of 3,4-dihydroxybenzaldehyde (50 g, 362 mmol) and powdered potassium carbonate (50 g, 362 mol) in dimethylformamide (250 mL) was heated at 100° C. under an atmosphere of chlorodifluoromethane using a −78° C. condenser for 5.5 h. An additional quantity of potassium carbonate (10 g) was added and the reaction was continued for another 0.5 h. The mixture was allowed to cool, was acidified to pH 5–6 with concentrated hydrochloric acid and was concentrated under reduced pressure. The residue was partitioned between ether and 3N aqueous hydrochloride and was extracted five times with ether. The organic extract was dried (magnesium sulfate) and the solvent was removed in vacuo. The residue was purified by flash chromatography, eluting with 2:1 hexanes/ethyl acetate, providing a yellow solid, which was triturated with ethyl acetate/hexanes to provide, in three crops, a white solid (12.1 g, 18%): m.p. 84°–86° C.

5b. 3-Cyclopentyloxy-4-difluoromethoxybenzaldehyde To a mixture of 3-hydroxy-4-difluoromethoxybenzaldehyde (2.9 g, 15 mmol) and powdered potassium carbonate (3.2 g, 23 mmol) in dimethylformamide (15 mL) under an argon atmosphere was added bromocyclopentane (2.5 mL, 23 mmol) and the mixture was stirred and heated at 50° C. for 1 h and at 80°–85° C. for 1.5 h. The mixture was allowed to cool and was partitioned between ethyl acetate and water. The organic extract was washed three times with water, was dried (sodium sulfate) and the solvent was removed in vacuo. Purification by flash chromatography, eluting with 20–30% ether/hexanes, provided a yellow solid (3.5 g, 89%).

5c. (3-Cyclopentyloxy-4-difluoromethoxyphenyl) acetonitrile To a solution of (3-cyclopentyloxy-4-difluoromethoxyphenyl)benzaldehyde (3.4 g, 13.4 mmol) in absolute ethanol (33 mL) under an argon atmosphere at room temperature was added sodium borohydride (1.06 g, 28 mmol). After 20 min, 10% aqueous sodium hydroxide (15 mL) was added, the ethanol was removed in vacuo and the aqueous residue was extracted three times with ether. The organic extract was washed twice with brine, was dried (magnesium sulfate) and evaporated to a pale yellow oil (3.44 g). A solution of this alcohol (1.52 g, 5.89 mmol) and pyridine (0.48 mL, 6 mmol) in alumina-dried chloroform (15 mL) under an argon atmosphere was treated with thionyl chloride (0.52 mL, 7.08 mmol) and the mixture was heated at reflux for 1 h. The solvent was removed, ether was added and the precipitate was removed by filtration. The filtrate was concentrated to a pale yellow oil, which was dissolved in dimethylformamide (10 mL) under an argon atmosphere and treated with sodium cyanide (0.58 g, 11.8 mmol). After stirring at room temperature for 72 h, the mixture was partitioned between 5% aqueous sodium carbonate and ether. The organic extract was washed four times with water, was dried (potassium carbonate) and evaporated. Purification by flash chromatography, eluting with 15–20% ethyl acetate/hexanes, provided a pale yellow solid (3.2 g, 90%): m.p. 39°–41° C.

5d. Dimethyl4-cyano-4-(3-cyclopentyloxy-4-difluoromethoxyphenyl)pimelate To a solution of (3-cyclopentyloxy-4-difluoromethoxyphenyl)acetonitrile (1.8 g, 6.7 mmol) in acetonitrile (35 mL) under an argon atmosphere was added a 40% solution of Triton-B in methanol (0.31 mL, 0.67 mmol). The resulting mixture was heated to reflux and methyl acrylate (6.1 mL, 67.2 mmol) was added cautiously. After another 20 min, the reaction was cooled to room temperature and concentrated. The residue was partitioned between aqueous hydrochloric acid and ether, the organic layer was dried (magnesium sulfate) and evaporated to an oil (3.1 g, 100%).

5e. 2-Carbomethoxy-4-cyano-4-(3-cyclopentyloxy-4-difluoromethoxyphenyl)cyclohexan-1-one To a solution of dimethyl 4-cyano-4-(3-cyclopentyloxy-4-difluoromethoxyphenyl)pimelate (3.1 g, 6.7 mmol) in dry 1,2-dimethoxyethane (50 mL) under an argon atmosphere was added sodium hydride (80% dispersion in mineral oil, 0.81 g, 27 mmol). The resulting mixture was refluxed for 20 min, additional 1,2-dimethoxyethane (50 mL) was added and the mixture was refluxed for another 70 min. The mixture was cooled to 0° C., was acidified with dilute hydrochloric acid and was concentrated The mixture was partitioned between ether and dilute hydrochloric acid, the organic layer was dried (magnesium sulfate) and the solvent was removed in vacuo. The product was purified by flash chromatography, eluting with 85:15 hexanes/ethyl acetate, to provide a white solid (0.76 g, 37%): m.p. 109°–110.5° C.

Analysis Calc. for $C_{21}H_{23}F_2NO_5$: C 61.91, H 5.69, N 3.44; found: C 61.83, H 5.66, N 3.39.

EXAMPLE 6

2-Carbomethoxy-4-cyano-4-(3-cyclopropylmethoxy-4-difluoromethoxyphenyl)cyclohexan-1-one 6a. 3-Cyclopropylmethoxy-4-difluoromethoxybenzaldehyde To a mixture of 3-hydroxy-4-difluoromethoxybenzaldehyde (19.55 g, 104 mmol) and potassium carbonate (21.56 g, 156 mmol) in dimethylformamide (150 mL) under an argon atmosphere at 60° C. was added bromomethylcyclopropane (15.13 mL, 156 mmol) and the mixture was stirred and heated at 65° C. After 1.5 h, the mixture was allowed to cool and was filtered. The filtrate was concentrated under reduced pressure and the residue was partitioned between ethyl acetate and water and was extracted four times with ethyl acetate. The organic extract was washed twice with water and was dried (sodium sulfate). The solvent was removed in vacuo to provide an oil (26.4 g).

6b. 3-Cyclopropylmethoxy-4-difluoromethoxybenzyl alcohol Crude 3-cyclopropylmethoxy-4-difluoromethoxybenzaldehyde (26.4 g) in absolute ethanol (200 mL) was treated with sodium borohydride (8.23 g, 217 mmol) under an argon atmosphere at room temperature for 0.33 h. Ten percent aqueous sodium hydroxide (150 mL) was added, the ethanol was removed in vacuo and the aqueous residue was extracted three times with ether. The organic extract was washed twice with brine, was dried (sodium sulfate), was filtered and was evaporated to a pale yellow oil (24.4 g).

6c. 3-Cyclopropylmethoxy-4-difluoromethoxybenzyl chloride A solution of crude 3-cyclopropylmethoxy-4-difluoromethoxybenzyl alcohol (24.4 g) and pyridine (9.8 mL, 120 mmol) in chloroform (150 mL) under an argon atmosphere was treated with thionyl chloride (8.0 mL, 110 mmol) and the mixture was heated at reflux for 1 h. The solvent was removed, ether was added and the precipitate was removed by filtration. The filtrate was concentrated to a pale yellow oil (26 g).

6d. (3-Cyclopropylmethoxy-4-difluoromethoxyphenyl) acetonitrile To 3-cyclopropylmethoxy-4-difluoromethoxybenzyl chloride (26 g) in dimethylformamide (150 mL) under an argon atmosphere was added sodium cyanide (9.7 g, 198 mmol). The resulting mixture was stirred at room temperature and heated gently for 2 h, then cooled and concentrated. The mixture was partitioned between basic brine and ether and extracted twice. The organic extract was washed with brine and was dried (sodium sulfate). The solvent was removed in vacuo to provide an orange-brown oil (24 g), which was used without purification.

6e. Dimethyl 4-cyano-4-(3-cyclopropylmethoxy-4-difluoromethoxyphenyl)pimelate To a solution of crude (3-cyclopropylmethoxy-4-difluoromethoxyphenyl) acetonitrile (24 g) in acetonitrile (500 mL) under an argon atmosphere was added a 40% solution of Triton-B in methanol (4.3 mL, 9.5 mmol). The resulting mixture was heated to reflux and methyl acrylate (43 mL, 470 mmol) was added cautiously. After 20 min, the reaction was cooled to room temperature and water and dilute hydrochloric acid were added and the mixture was concentrated The residue was partitioned between water and ether, the organic layer was dried (magnesium sulfate) and evaporated to an orange-brown oil (41 g).

6f. 2-Carbomethoxy-4-cyano-4-(3-cyclopropylmethoxy-4-difluoromethoxyphenyl)cyclohexan-1-one To a suspension of sodium hydride (80% dispersion in mineral oil, 11.6 g, 388 mmol) in dry 1,2-dimethoxyethane (700 mL) under an argon atmosphere was added a solution of crude dimethyl 4-cyano-4-(3-cyclopropylmethoxy-4-difluoromethoxyphenyl)pimelate (41 g) in dry 1,2-dimethoxyethane (700 mL). The resulting mixture was heated at 60° C. for 1 h, cooled to room temperature, quenched with dilute aqueous hydrochloric acid and concentrated The residue was diluted with water, was acidified to pH 3 and was extracted twice with methylene chloride. The organic extract was washed with acidic water, was dried (sodium sulfate) and the solvent was removed in vacuo. Purification by flash chromatography, eluting with methylene chloride, followed by trituration with cold ether provided a solid (17.7 g, 43% from 3-cyclopropylmethoxy-4-difluoromethoxybenzaldehyde): m.p. 115°–116° C.

Analysis Calc. for $C_{20}H_{21}F_2NO_5$: C 61.06, H 5.38, N 3.56; found: C 61.16, H 5.40, N 3.52.

EXAMPLE 7

4-Cyano-4-(3-cyclopentyloxy-4-methoxyphenyl) cyclohexan-1-one

A mixture of 2-carbomethoxy-4-cyano-4-(3-cyclopentyloxy-4-methoxyphenyl)cyclohexan-1-one (0.80 g, 2.15 mmol), dimethyl sulfoxide (16 mL), water (1 mL) and sodium chloride (0.8 g) under an argon atmosphere was heated at 140°–145° C. for 5 h. The reaction mixture was cooled and concentrated The residue was purified by flash chromatography, eluting with 3:1 hexanes/ethyl acetate, to provide a yellow solid. Trituration with hexanes/ethyl acetate yielded a white solid (0.52 g, 77%): m.p. 111°–112° C.

Analysis Calc. for $C_{19}H_{23}NO_3$: C 72.82, H 7.40, N 4.47; found: C 72.72, H 7.39, N 4.48.

EXAMPLE 8

4-(3,4-Bisdifluoromethoxyphenyl)-4-cyanocyclohexan-1-one

A mixture of 2-carbomethoxy-4-(3,4-bisdifluoromethoxyphenyl)-4-cyanocyclohexan-1-one (0.55 g, 1.4 mmole), dimethyl sulfoxide (8 mL), water (0.5 mL) and sodium chloride (0.5 g) under an argon atmosphere was heated at 140°–145° C. for 4 h. The reaction mixture was cooled to room temperature and concentrated. The residue was partitioned between ether and water, the organic layer was dried (magnesium sulfate) and the solvent was removed in vacuo. The product was purified by flash chromatography, eluting with 1:1 hexanes/ether. The residue was partitioned between water and ethyl acetate and the organic layer was evaporated to yield a yellow solid. Trituration from the minimal amount of ethyl acetate/hexanes provided a solid (0.3 g, 63.6%): m.p. 64°–66° C.

Analysis Calc. for $C_{15}H_{13}NO_3F_4$: C 54.39, H 3.96, N 4.23; found: C 54.25, H 3.96, N 4.20.

EXAMPLE 9

4-Cyano-(3-difluoromethoxy-4-methoxyphenyl) cyclohexan-1-one

A mixture of 2-carbomethoxy-4-cyano-4-(3-difluoromethoxy-4-methoxyphenyl)cyclohexan-1-one (0.51 g, 1.44 mmole), dimethyl sulfoxide (11 mL), water (1 mL) and sodium chloride (0.53 g) under an argon atmosphere was heated at 150° C. for 5 h. The reaction mixture was partitioned between ethyl acetate and water and extracted tree times with ethyl acetate. The combined organic extract was washed twice with water, once with brine, was dried (potassium carbonate) and the solvent was removed in vacuo. The product was purified by flash chromatography, eluting with 2:1 hexanes/ethyl acetate, to provide an oil (0.36 g, 85%).

Analysis Calc. for $C_{15}H_{15}NO_3F_2 \cdot \frac{1}{8}H_2O$: C 60.55, H 5.17, N 4.71; found: C 60.42, H 5.07, N 4.77.

EXAMPLE 10

4-Cyano-(3-cyclopropylmethoxy-4-methoxyphenyl) cyclohexan-1-one

A mixture of 2-carbomethoxy-4-cyano-4-(3-cyclopropylmethoxy-4-methoxyphenyl)cyclohexan-1-one (1.7 g, 4.7 mmole), dimethyl sulfoxide (34 mL), water (3 mL) and sodium chloride (1.6 g) under an argon atmosphere was heated at 150° C. for 4 h, was stirred at room temperature overnight and was concentrated. The residue was partitioned between ethyl acetate and water and extracted three times with ethyl acetate. The combined organic extract was washed twice with water, once with brine, was dried (magnesium sulfate) and the solvent was removed in vacuo. The product was purified by flash chromatography, eluting with 2:1 hexanes/ethyl acetate, to provide a solid (1.09 g, 77%): m.p. 116°–118° C.

Analysis Calc. for $C_{18}H_{21}NO_3 \cdot \frac{1}{8}H_2O$: C 71.68, H 7.10, N 4.64; found: C 71.51, H 7.03, N 4.55.

EXAMPLE 11

4-Cyano-4-(3-cyclopentyloxy-4-difluoromethoxyphenyl)cyclohexan-1-one

A mixture of 2-carbomethoxy-4-cyano-4-(3-cyclopentyloxy-4-difluoromethoxyphenyl)cyclohexan-1-one (0.98 g, 2.4 mmole), dimethyl sulfoxide (10 mL), water (0.62 mL) and sodium chloride (0.62 g) under an argon atmosphere was heated at 145° C. for 5 h. The reaction mixture was cooled to room temperature and concentrated. The residue was partitioned between ether and water, the organic layer washed with water, was dried (magnesium sulfate) and the solvent was removed in vacuo. The product was purified by flash chromatography, eluting with 20–30% ethyl acetate/hexanes. The isolated residue was dissolved in ethyl acetate, this was washed twice with dilute sodium hydroxide, once with water, once with brine and then was dried and evaporated to yield a solid (0.2 g, 23.6%): m.p. 76°–78.5° C.

Analysis Calc. for $C_{19}H_{21}F_2NO_3 \cdot \frac{1}{8}H_2O$: C 64.76, H 6.10, N 3.97; found: C 64.76, H 6.04, N 3.89.

EXAMPLE 12

4-Cyano-4-(3-cyclopropylmethoxy-4-difluoromethoxyphenyl)cyclohexan-1-one

A mixture of 2-carbomethoxy-4-cyano-4-(3-cyclopentyloxy-4-difluoromethoxyphenyl)cyclohexan- 1-one (0.5 g, 1.27 mmole), dimethyl sulfoxide (10 mL), water (1 mL) and sodium chloride (0.5 g) under an argon atmosphere was heated at 145°–150° C. for 4.5 h. The reaction mixture was cooled to room temperature and concentrated. The residue was partitioned between ethyl acetate and water, extracted twice with ethyl acetate, the organic layer was washed twice with water and once with brine, was dried (sodium sulfate) and the solvent was removed in vacuo. The product was purified by flash chromatography, eluting with 20–25% ethyl acetate/hexanes, and the resultant solid was triturated with ether/hexane and then with cold ether to provide a solid (0.22 g, 51.6%): m.p. 85.5°–86.5° C.

Analysis Calc. for $C_{18}H_{19}F_2NO_3$: C 64.47, H 5.71, N 4.18; found: C 64.28, H 5.63, N 4.20.

EXAMPLE 13

4-Cyano-4-(3-cyclopentyloxy-4-methoxyphenyl) cyclohexan-1-one oxime

To a solution of 4-cyano-4-(3-cyclopentyloxy-4-methoxyphenyl)cyclohexan-1-one (0.125 g, 0.4 mmol) in pyridine (2 mL) was added hydroxylamine hydrochloride (0.031 g, 0.44 mmol), the mixture was stirred at room temperature under an argon atmosphere for 4 h and the solvent was evaporated. The mixture was partitioned between water and ethyl acetate, was extracted twice with ethyl acetate, the organic extract was dried (potassium carbonate) and the solvent was removed in vacuo. Purification by flash chromatography, eluting with 25% ethyl acetate/hexanes, followed by trituration of the product with ether/hexanes provided a white solid (0.125 g, 95%): m.p. 50°–53° C.

Analysis Calc. for $C_{19}H_{24}N_2O_3$: C 69.44, H 7.37, N 8.53; found: C 69.35, H 7.47, N 8.28.

EXAMPLE 14

4-(3-Cyclopentyloxy-4-methoxyphenyl)-4-formylcyclohexan-1-one 14a. 4-Cyano-4-(3-cyclopentyloxy-4-methoxyphenyl) cyclohexan-1-one dimethyl ketal A mixture of 4-cyano-4-(3-cyclopentyloxy-4-methoxyphenyl)cyclohexan-1-one (0.5 g, 1.6 mmol), trimethyl orthoformate (0.21 mL, 1.9 mmol) and a catalytic amount of p-toluenesulfonic acid in methanol (20 mL) was heated gently under an argon atmosphere for 2 h. The mixture was cooled, was partitioned between aqueous sodium carbonate and ethyl acetate, was extracted twice with ethyl acetate, the organic extract was dried (potassium carbonate) and the solvent was removed in vacuo to provide an oil (0.57 g, 99%).

14b. 4-(3-Cyclopentyloxy-4-methoxyphenyl)-4-formylcyclohexan-1-one dimethyl ketal A solution of 4-cyano-4-(3-cyclopentyloxy-4-methoxyphenyl) cyclohexan-1-one dimethyl ketal (0.57 g, 1.6 mmol) in toluene (20 mL) at room temperature under an argon atmosphere was treated with a solution of diisobutylaluminum hydride (1.5M in toluene, 2.7 mL, 4 mmol). After 2 h, a solution of saturated aqueous sodium bisulfite was added and the mixture was extracted twice with ethyl acetate. The organic extract was washed with 5% aqueous sodium carbonate, was dried (potassium carbonate) and the solvent was removed in vacuo to provide an oil (0.55 g, 96%).

14c. 4-(3-Cyclopentyloxy-4-methoxyphenyl)-4-formylcyclohexan-1-one 4-(3-Cyclopentyloxy-4-methoxyphenyl)-4-formylcyclohexan-1-one dimethyl ketal (0.1 g, 0.28 mmol) in ethyl acetate (2 mL) was treated with 3N hydrochloric acid (5 mnL) and the mixture was stirred vigorously and gently heated for 10 min. The mixture was extracted twice with ethyl acetate, the combined organic extracts were washed with 5% aqueous sodium carbonate, dried (potassium carbonate) and the solvent was removed in vacuo. This material, combined with that obtained from an identical reaction, was purified by flash chromatography, eluting with 2% ethyl acetate/chloroform, to provide a white solid (0.1 g, 57%): m.p. 55°–57° C.

Analysis Calc. for $C_{19}H_{24}O_4$: C 72.13, H 7.65; found: C 72.09, H 7.57.

EXAMPLE 15

4-(3-Cyclopentyloxy-4-methoxyphenyl)-4-(hydroxymethyl)cyclohexan-1-one 15a. 4-(3-Cyclopentyloxy-4-methoxyphenyl)-4-(hydroxymethyl)cyclohexan-1-one-dimethyl ketal To a solution of 4-(3-cyclopentyloxy-4-methoxyphenyl)-4-formylcyclohexan-1-one dimethyl ketal (0.24 g, 0.66 mmol) in 1,2-dimethoxy-ethane (5 mL) under an argon atmosphere was added sodium borohydride (0.05 g, 1.3 mmol) and the mixture was stirred at room temperature for 0.75 h. Water was added, the mixture was partitioned between ether and water, was extracted twice with ether, the organic extract was dried (potassium carbonate) and evaporated to an oil (0.19 g, 79%).

15 b. 4-(3-Cyclopentyloxy-4-methoxyphenyl)-4-(hydroxymethyl)cyclohexan-1-one 4-(3-Cyclopentyloxy-4-methoxyphenyl)-4 (hydroxymethyl)cyclohexan-1-one dimethyl ketal (0.15 g, 0.41 mmol) in ether (2 mL) was treated with 1N hydrochloric acid (2 mL) and the mixture was snared vigorously and gently heated for 10 min. The mixture was extracted with ether, the combined organic extracts were washed with 5% aqueous sodium carbonate, dried (potassium carbonate) and the solvent was removed in vacuo. Purification by flash chromatography, eluting with 25% ethyl acetate/chloroform, provided a wax (0.06 g, 56%).

Analysis Calc. for $C_{19}H_{26}O_4$: C 71.67, H 8.23; found: C 71.81, H 8.19.

EXAMPLE 16

4-(3-Cyclopentyloxy-4-methoxyphenyl)-4-(fluoromethyl)cyclohexan-1-one 16a. 4-(3-Cyclopentyloxy-4-methoxyphenyl)-4-(fluoromethyl)cyclohexan-1-one dimethyl ketal A solution of 4-(3-cyclopentyloxy-4-methoxyphenyl)-4-(hydroxymethyl)cyclohexan-1-one dimethyl ketal (0.37 g, 1.02 mmol) in methylene chloride (5 mL) was added dropwise to a solution of diethylaminosulfur trifluoride (0.14 mL, 1.02 mmol) at −78° C. under an argon atmosphere. The mixture was allowed to warm to room temperature and after 0.75 h, 5% aqueous sodium carbonate was added. The mixture was extracted with chloroform, the organic extract was dried (magnesium sulfate) and the solvent was removed in vacuo to provide a yellow oil (0.3 g, 80%).

16b. 4-(3-Cyclopentyloxy-4-methoxyphenyl)-4-(fluoromethyl)cyclohexan-1-one 4-(3-Cyclopentyloxy-4-methoxyphenyl)-4-(fluoromethyl)cyclohexan-1-one dimethyl ketal (0.35 g, 0.95 mmol) in ethyl acetate (2 mL) was treated with 1N hydrochloric acid (2 mL) and the mixture was stirred vigorously and gently heated for 10 min. The mixture was extracted with ethyl acetate, the organic extract was washed with 5% aqueous sodium carbonate, dried (magnesium sulfate) and the solvent was removed in vacuo. Purification by flash chromatography, eluting with 25% ethyl acetate/hexanes, followed by trituration with ether/hexanes, provided a white solid (0.075 g, 24%): m.p. 72°–74° C.

Analysis Calc. for $C_{19}H_{25}FO_3$: C 71.23, H 7.87; found: C 71.22, H 7.70.

EXAMPLE 17

4-Aminocarbonyl-4-(3-cyclopentyloxy-4-methoxyphenyl)cyclohexan-1-one 17a. 4-Aminocarbonyl-4-(3-cyclopentyloxy-4-methoxyphenyl)cyclohexan-1-one dimethyl ketal A solution of 4-cyano-4-(3-cyclopentyloxy-4-methoxyphenyl)cyclohexan-1-one dimethyl ketal (0.34 g, 0.95 mmol) and powdered potassium carbonate (0.7 g, 5.1 mmol) in methanol (20 mL) and water (4 mL) at 0° C. was treated with hydrogen peroxide (30% solution, 2.55 mL). The mixture was allowed to warm to room temperature and, after seven days, brine was added and the mixture was extracted with methylene chloride. The organic extract was washed twice with brine, dried (potassium carbonate) and the solvent was removed in vacuo. Purification by flash chromatography provided the amide (0.055 g, 15%) along with recovered starting material (0.25 g).

17b. 4-Aminocarbonyl-4-(3-cyclopentyloxy-4-methoxyphenyl)cyclohexan-1-one A mixture of 4-aminocarbonyl-4-(3-cyclopentyloxy-4-methoxyphenyl)cyclohex-1-one dimethyl ketal (0.055 g, 0.15 mmol) and p-toluenesulfonic acid (catalytic amount) in 20% aqueous acetone (5 mL) was stirred under an argon atmosphere at reflux for 8 h. The mixture was cooled, diluted with water and extracted with methylene chloride. The organic extract was dried (magnesium sulfate) and the solvent was removed in vacuo to provide a hygroscopic, amorphous material (0.035 g, 72%).

Analysis Calc. for $C_{19}H_{25}NO_4 \cdot \frac{3}{8}H_2O$: C 67.48, H 7.67, N 4.14; found: C 67.38, H 7.54, N 3.86.

EXAMPLE 18

4-(3-Cyclopentyloxy-4-methoxyphenyl)-4-ethynylcyclohexan-1-one 18a. 4-(3-Cyclopentyloxy-4-methoxyphenyl)-4-ethynylcyclohexan-1-one dimethyl ketal To a solution of potassium t-butoxide (0.155 g, 1.38 mmol) in dry tetrahydrofuran (5 mL) under an argon atmosphere at –78° C. was added a solution of dimethyl (diazomethyl)phosphonate (ca. 88% pure, 0.24 g, 1.38 mmol). After 0.25 h, a solution of 4-(3-cyclopentyloxy-4-methoxyphenyl)-4-formylcyclohexan-1-one dimethyl ketal (0.42 g, 1.15 mmol) in dry tetrahydrofuran (5 mL) was added dropwise and the mixture was allowed to stir at –78° C. under an argon atmosphere for 5 h. Aqueous acetic acid was added, the mixture was concentrated, partitioned between methylene chloride and water and extracted twice. The organic extract was dried (magnesium sulfate) and evaporated. Purification by flash chromatography, eluting with 3:1 hexanes/ethyl acetate, provided an oil (0.13 g, 32%).

18b. 4-(3-Cyclopentyloxy-4-methoxyphenyl)-4-ethynylcyclohexan-1-one A mixture of 4-(3-cyclopentyloxy-4-methoxyphenyl)-4-ethynylcyclohex-1-one dimethyl ketal (0.13 g, 0.36 mmol) and p-toluenesulfonic acid (catalytic amount) in acetone (5 mL) was stirred under an argon atmosphere at room temperature for 1.5 h. The mixture was concentrated, diluted with ethyl acetate and washed with water. The organic extract was dried (magnesium sulfate) and the solvent was removed in vacuo to provide an oil (0.11 g, 97%).

Analysis Calc. for $C_{20}H_{24}O_3 \cdot \frac{1}{2}H_2O$: C 74.74, H 7.84; found: C 74.81, H 7.84.

EXAMPLE 19

4-(3,4-Bisdifluoromethoxyphenyl)-4-ethynylcyclohexan-1-one 19a. 4-(3,4-Bisdifluoromethoxyphenyl)-4-cyanocyclohexan-1-one dimethyl ketal A mixture of 4-cyano-4-(3,4-bisdifluoromethoxyphenyl)cyclohexan-1-one (1.34 g, 4.05 mmol), trimethyl orthoformate (0.53 mL, 4.85 mmol) and a catalytic amount of p-toluenesulfonic acid in methanol (40 mL) was heated gently under an argon atmosphere for 2 h. The mixture was cooled and then concentrated The residue was partitioned between 5% aqueous sodium carbonate and ethyl acetate, was extracted twice with ethyl acetate, the organic extract was dried (potassium carbonate) and the solvent was removed in vacuo to provide an oil (1.5 g, 98%).

19b. 4-(3,4-Bisdifluoromethoxyphenyl)-4-formylcyclohexan-1-one dimethyl ketal A solution of 4-cyano-4-(3,4-bisdifluoromethoxyphenyl)cyclohexan-1-one dimethyl ketal (1.5 g, 3.98 mmol) in toluene (50 mL) at room temperature under an argon atmosphere was treated with a solution of diisobutylaluminum hydride (1M in toluene, 10 mL, 10 mmol). After 4 h, a solution of saturated aqueous sodium bisulfite was added and the mixture was extracted twice with ethyl acetate. The combined organic extract was dried (potassium carbonate) and the solvent was removed in vacuo to provide an oil (1.5 g, 99%).

19c. 4-(3,4-Bisdifluoromethoxy)-4-ethynylcyclohex-1-one dimethyl ketal To a suspension of potassium t-butoxide (0.18 g, 1.6 mmol) in dry tetrahydrofuran (5 mL) under an argon atmosphere at –78° C. was added a solution of dimethyl (diazomethyl)phosphonate (ca. 90% pure, 0.27 g, 1.6 mmol) in tetrahydrofuran (5 mL). After 0.25 h, a solution of 4-(3,4-bisdifluoromethoxyphenyl)-4-formylcyclohexan-1-one dimethyl ketal (0.5 g, 1.3 mmol) in dry tetrahydrofuran (5 mL) was added dropwise and the mixture was allowed to stir at –78° C. under an argon atmosphere for 10 min. Aqueous acetic acid was added, the mixture was concentrated and was partitioned between methylene chloride and water. The organic extract was dried (magnesium sulfate) and evaporated. Purification by flash chromatography, eluting with 3:1 hexanes/ethyl acetate, provided an oil (0.2 g, 41%).

19d. 4-(3,4-Bisdifluoromethoxyphenyl)-4-ethynylcyclohexan-1-one A mixture of 4-(3,4-bisdifluoromethoxyphenyl)-4-ethynylcyclohex-1-one dimethyl ketal (0.2 g, 0.53 mmol) and p-toluenesulfonic acid (catalytic amount) in acetone (10 mL) was stirred under an argon atmosphere at room temperature for 0.5 h. The mixture was concentrated, was diluted with methylene chloride and was washed with water. The organic extract was dried (magnesium sulfate) and the solvent was removed in vacuo to provide an oil (0.17 g, 98%).

Analysis Calc. for $C_{16}H_{14}F_4O_3$: C 58.19, H 4.27; found: C 58.30, H 4.40.

EXAMPLE 20

4-(3,4-Bisdifluoromethoxyphenyl)-4-(oxamidomethyl)cyclohexan-1-one 20a. 4-Aminomethyl-4-(3,4-bisdifluoromethoxyphenyl)cyclohexan-1-one dimethyl ketal A solution of 4-(3,4-bisdifluoromethoxyphenyl)-4-cyanocyclohexan-1-one dimethyl ketal (0.5 g, 1.33 mmol) in tetrahydrofuran (3 mL) at room temperature under an argon atmosphere was added to a suspension of lithium aluminum hydride (0.1 g, 2.66 mmol) in tetrahydrofuran (4.5 mL). After 6 h, ethyl acetate and saturated aqueous sodium potassium tartrate were added, followed by saturated aqueous sodium carbonate, and the mixture was extracted four times with ethyl acetate. The organic extract was dried (potassium carbonate) and the solvent was removed in vacuo to provide an oil (0.43 g, 85%).

20b. 4-(3,4-Bisdifluoromethoxyphenyl)-4-(oxamidomethyl)cyclohexan-1-one To a solution of 4-aminomethyl-4-(3,4-bisdifluoromethoxyphenyl)cyclohexan-1-one dimethyl ketal (0.43 g, 1.13 mmol) and triethylamine (0.16 mL, 1.13 mmol) in methylene chloride (7 mL) under an argon atmosphere at −78°C. was added methyl oxalyl chloride (0.12 mL, 1.07 mmol). After 5 min, water was added and the mixture was partitioned between methylene chloride and acidic water and was extracted twice. The organic extract was dried (potassium carbonate) and evaporated to an oil (0.59 g). This oil in methanol (ca. 2 mL) in a pressure tube was cooled to −78° C. and an equal volume of anhydrous ammonia was condensed into the tube. The tube was sealed, was allowed to come to room temperature and was stirred under pressure for 6 h. The ammonia was allowed to evaporate, the mixture was partitioned between chloroform and water and was extracted three times. The organic extract was dried (potassium carbonate) and evaporated to the ketal, an oil (0.6 g). This oil in tetrahydrofuran (13 mL) was treated with 5% hydrochloric acid (7.6 mL) and the mixture was stirred under an argon atmosphere at room temperature for 20 h. The mixture was poured into acidic water, was extracted three times with methylene chloride, the organic extract was dried (potassium carbonate) and the solvent was removed in vacuo. Purification by flash chromatography, eluting with 5% ether/chloroform, followed by trituration with ether/methylene chloride, provided a white solid (0.21 g, 45%): m.p. 164°–165° C.

Analysis Calc. for $C_{17}H_{18}F_4N_2O_5$: C 50.25, H 4.47, N 6.89; found: C 50.04, H 4.45, N 6.64.

EXAMPLE 21

4-Cyano-4-(3-cyclopropylmethoxy-4-difluoromethoxyphenyl)-2-[2-(trimethylsilyl)ethoxycarbonyl)]cyclohexan-1-one A solution of 2-carbomethoxy-4-cyano-4-(3-cyclopropylmethoxy-4-difluoromethoxyphenyl)cyclohexan-1-one (0.18 g, 0.45 mmol) in 2-(trimethylsilyl)-ethanol (1.0 mL) was heated at 180° C. under an argon atmosphere for 2.5 h. The mixture was cooled, was concentrated and the product was purified by flash chromatography, eluting with 3:1 hexanes/ether, to provide a colorless oil (0.2 g, 95%).

EXAMPLE 22

4-Cyano-4-[3-cyclopentyloxy-4-(4-fluorobenzyloxy)phenyl]cyclohexan-1-one

A solution of 4-cyano-4-[3-cyclopentyloxy-4-methoxyphenyl)cyclohexan-1-one (0.75 g, 2.4 mmol) and concentrated hydrochloric acid (2 mL) in methanol (10 mL) was heated at reflux under an argon atmosphere for 2 h. The mixture was cooled, was diluted with water and was extracted three times with methylene chloride. The organic extract was dried (magnesium sulfate) and was evaporated to the phenol (0.54 g, 92%). A vigorously stirred mixture of this phenol, 4-fluorobenzyl bromide (0.83 mL, 6.6 mmol) and potassium carbonate (0.92 g, 6.6 mmol) in dimethylformamide (12 mL) was heated under an argon atmosphere at 90° C. for 2 h. The mixture was allowed to cool, was diluted with water and was extracted three times with ether. The organic extract was dried (magnesium sulfate) and the solvent was removed in vacuo. Purification by flash chromatography, eluting with 30% ethyl acetate/hexanes, provided a white solid (0.6 g, 78%): m.p. 145°–146° C.

Analysis Calc. for $C_{21}H_{20}FNO_3 \cdot \frac{1}{5}H_2O$: C 70.65, H 5.76, N 3.92; found: C 70.59, H 5.59, N 3.99.

EXAMPLE 23

4-Cyano-4-[3-cyclopentyloxy-4-(4-fluorobenzyloxy)phenyl]cyclohexan-1-one oxime

A solution of 4-cyano-4-[3-cyclopentyloxy-4-(4-fluorobenzyloxy)phenyl)cyclohexan-1-one (0.525 g, 1.49 mmol) and hydroxylamine hydrochloride (0.114 g, 1.63 mmol) in pyridine (5 mL) was was stirred at room temperature under an argon atmosphere for 18 h. The mixture was partitioned between 1N hydrochloric acid and methylene chloride, the organic extract was dried (magnesium sulfate) and the solvent was removed in vacuo. Purification by flash chromatography, eluting with 35% ethyl acetate/hexanes, provided a white solid (0.45 g, 82%): m.p. 55°–57° C.

EXAMPLE 24

4-(3-Cyclopropylmethoxy-4-difluoromethoxyphenyl)-4-ethynylcyclohexan-1-one

The title compound, prepared substantially as described above for 4-(3,4-bisdifluoromethoxyphenyl)-4-ethynylcyclohexan-1-one in EXAMPLE 19, was isolated as a solid: m.p. 75°–77° C.

Analysis Calc. for $C_{19}H_{20}F_2O_3$: C 68.25, H 6.03; found: C 67.93, H 6.10.

EXAMPLE 25

4-Cyano-4-(3-cyclopropylmethoxy-4-methoxyphenyl)cyclohexan-1-one oxime

The title compound, prepared substantially as described above for 4-cyano-4-(3-cyclopentyloxy-4-methoxyphenyl)cyclohexan-1-one oxime in EXAMPLE 13, was isolated as a solid: m.p. 75°–77° C.

Analysis Calc. for $C_{18}H_{22}N_2O_3 \cdot \frac{1}{4}H_2O$: C 67.80, H 7.11, N 8.78; found: C 68.03, H 7.08, N 8.59.

EXAMPLE 26

2-Aminocarbonyl-4-cyano-4-(3-cyclopropylmethoxy-4-methoxyphenyl)cyclohexan-1-one 26a. 2-Carbomethoxy-4-cyano-4-(3-cyclopropylmethoxy-4-methoxyphenyl)-1-(methoxymethyloxy)cyclohex-1-ene A solution of 2-carbomethoxy-4-cyano-4-(3-cyclopropylmethoxy-4-methoxyphenyl)cyclohexan-1-one (1.0 g, 2.8 mmol) and sodium hydride (80% dispersion in mineral oil, 0.09 g, 3.1 mmol) in dry hexamethylphosphoric triamide (8 mL) was stirred under an argon atmosphere at room temperature for 0.5 h. Chloromethylmethyl ether (0.26 mL, 3.4 mmol) was added and stirring was continued for 4.5 h. The mixture was partitioned between ethyl acetate and saturated aqueous sodium bicarbonate, was extracted three times, the organic layer was dried (sodium sulfate) and the solvent was removed in vacuo. The product was purified by flash chromatography, eluting with 3:1 hexanes/ethyl acetate, to provide a white solid (0.5 g, 44%): m.p. 98°–99° C.

26b. 2-Carboxy-4-cyano-4-(3-cyclopropylmethoxy-4-methoxyphenyl)-1-(methoxymethyloxy)cyclohex-1-ene A solution of 2-carbomethoxy-4-cyano-(3-cyclopropylmethoxy-4-methoxyphenyl)-1-(methoxymethyloxy)cyclohex-1-ene (0.5 g, 1.25 mmol) and potassium hydroxide (0.21 g, 3.75 mmol) in methanol (13 mL), tetrahydrofuran (5 mL) and water (7.5 mL) under an argon atmosphere was heated at 65° C. for 3 h. The mixture was partitioned between methylene chloride and acidic water, was extracted twice, the organic layer was dried (magnesium sulfate) and the solvent was removed in vacuo. Purification by flash chromatography, eluting with 5% methanol/chloroform, provided an oil (0.26 g, 54%).

26c. 2-Aminocarbonyl-4-cyano-4-(3-cyclopropylmethoxy-4-methoxyphenyl)-1-(methoxymethyloxy)cyclohex-1-ene A mixture of 2-carboxy-4-cyano-4-(3-cyclopropylmethoxy-4-methoxyphenyl)-1-(methoxymethyloxy)cyclohex-1-ene (0.26 g, 0.67 mmol), N-methyl morpholine (0.09 ml, 0.8 mmol) and isobutyl chloroformate (0.1 mL, 0.77 mmol) in dry 1,2-dimethoxyethane (7 mL) was stirred under an argon atmosphere at room temperature for 10 min. Ammonium hydroxide (0.07 mL, 1.0 mmol) was added and stirring was continued for 0.5 h. The mixture was partitioned between methylene chloride and 5% aqueous sodium carbonate, was extracted three times, the organic layer was dried (potassium carbonate) and the solvent was removed in vacuo to provide a white solid (0.22 g, 85%): m.p. 120°–122° C.

26d. 2-Aminocarbonyl-4-cyano-4-(3-cyclopropylmethoxy-4-methoxyphenyl)cyclohexan-1-one A solution of 2-aminocarbonyl-4-cyano-4-(3-cyclopropylmethoxy-4-methoxyphenyl)-1-(methoxymethyloxy)cyclohex-1-ene (0.22 g, 0.57 mmol) in 50% aqueous acetic acid (12 mL, containing 9 drops concentrated sulfuric acid per 30 mL) was heated at 75° C. under an argon atmosphere for 2 h. The mixture was cooled, was partitioned between methylene chloride and water, was extracted twice, the organic layer was dried (potassium carbonate) and the solvent was removed in vacuo. Purification by flash chromatography, eluting with 5% methanl/chloroform, followed by crystallization from ether/methylene chloride, provided a white powder (0.07 g, 51%): m.p. 154°–155° C.

Analysis Calc. for $C_{19}H_{22}N_2O_4 \cdot \frac{1}{2}H_2O$: C 64.94, H 6.60, N 7.97; found: C 64.93, H 6.56, N 7.61.

EXAMPLE 27

2-Carboxy-4-cyano-4-(3-cyclopropylmethoxy-4-difluoromethoxyphenyl)cyclohexan-1-one 27a. 4-Cyano-4-(3-cyclopropylmethoxy-4-difluoromethoxyphenyl)-2-[2-(trimethylsilyl)ethoxycarbonyl)]cyclohexan-1-one A solution of 2-carbomethoxy-4-cyano-4-(3-cyclopropylmethoxy-4-difluoromethoxyphenyl)cyclohexan-1-one (0.18 g, 0.45 mmol) in 2-(trimethylsilyl)ethanol (1.0 mL) was heated at 180° C. under an argon atmosphere for 2.5 h. The mixture was cooled, was concentrated and the product was purified by flash chromatography, eluting with 3:1 hexanes/ether, to provide a colorless oil (0.2 g, 95%).

27b. 2-Carboxy-4-cyano-4-(3-cyclopropylmethoxy-4-difluoromethoxyphenyl)-cyclohexan-1-one A solution of 4-cyano-4-(3-cyclopropylmethoxy-4-difluoromethoxyphenyl)-2-[2-(trimethylsilyl)ethoxycarbonyl)]cyclohexan-1-one (0.2 g, 0.42 mmol) and tetrabutylammonium fluoride (1M solution in tetrahydrofuran, 2 mL, 2 mmol) was stirred at room temperature under an argon atmosphere for 2.5 h. The mixture was poured into cold dilute aqueous hydrochloric acid, was extracted twice with ether, the organic extract was washed tee times with ice water, was dried (sodium sulfate) and the solvent was removed in vacuo. Trituration of the residue provided a white powder (0.12 g, 77%): m.p. 110°–112° C.(dec).

Analysis Calc. for $C_{19}H_{19}F_2NO_5$: C 60.16, H 5.05, N 3.69; found: C 60.25, H 5.07, N 3.57.

EXAMPLE 28

4-(3-Cyclopropylmethoxy-4-difluoromethoxyphenyl)-2,4-dicyanocyclohexan-1-one

To a stirred solution of 1-amino-4-(3-cyclopropylmethoxy-4-difluoromethoxyphenyl])-2,4-dicyanocyclohexan-1-ene (0.25 g, 0.696 mmol) in ethanol (2 mL) was added 6N hydrochloric acid (0.6 mL) and the mixture was stirred for 1.5 h at ambient temperature. The reaction was poured into ice water, was extracted three times with ether and the combined organic phase was washed with water, brine and was dried (sodium sulfate). The solvent was evaporated and the residue was purified by flash chromatography, eluting with 4% methanol/toluene, and the residue was triturated with ether to provide a white powder (0.08 g, 32%): m.p. 142°–143° C.

Analysis Calc. for $C_{19}H_{18}F_2N_2O_3 \cdot \frac{1}{4}H2O$: C 62.55, H 5.11, N 7.68; found: C 62.69, 62.39, H: 5.05, 5.04, N 7.47, 7.43.

EXAMPLE 29

2-Aminocarbonyl-4-cyano-4-(3-cyclopropylmethoxy-4-difluoromethoxyphenyl)cyclohexan-1-one 29a. 2-Carbomethoxy-4-cyano-4-(3-cyclopropylmethoxy-4-difluoromethoxyphenyl)-1-(methoxymethyloxy)cyclohex-1-ene The title compound, prepared substantially as described above for 2-carbomethoxy-4-cyano-4-(3-cyclopropylmethoxy-4-methoxyphenyl)-1-(methoxymethyloxy)cyclohex-1-ene in EXAMPLE 26a, was triturated with ether to provide white crystals (0.334 g, 77%): m.p. 81°–82.5° C.

Analysis Calc. for $C_{22}H_{25}F_2NO_6$: C 60.41, H 5.76, N 3.20; found: C 60.32, H 5.80, N 3.21.

29b. 2-Carboxy-4-cyano-4-(3-cyclopropylmethoxy-4-difluoromethoxyphenyl)-1-(methoxymethyloxy)cyclohex-1-ene The title compound, prepared substantially as described above for 2-carboxy-4-cyano-4-(3-cyclopropylmethoxy-4-methoxyphenyl)-1-(methoxymethyloxy)cyclohex-1-ene in EXAMPLE 26b, was isolated as an oil.

29c. 2-Aminocarbonyl-4-cyano-4-(3-cyclopropylmethoxy-4-difluoromethoxyphenyl)-1-(methoxymethyloxy)cyclohex-1-ene The title compound, prepared substantially as described above for 2-aminocarbonyl-4-cyano-4-(3-cyclopropylmethoxy-4-methoxyphenyl)-1-(methoxymethyloxy)cyclohex-1-ene in EXAMPLE 26c, was isolated as an oil.

29d. 2-Aminocarbonyl-4-cyano-4-(3-cyclopropylmethoxy-4-difluoromethoxyphenyl)-cyclohexan-1-one The title compound, prepared substantially as described above for 2-aminocarbonyl-4-cyano-4-

(3-cyclopropylmethoxy-4-methoxyphenyl)cyclohexan-1-one in EXAMPLE 26d, was isolated as a white powder (0.025 g, 24%): m.p. 157°–159° C.

Analysis Calc. for $C_{19}H_{20}F_2N_2O_4 \cdot \frac{1}{2}H_2O$: C 58.91, H 5.46, N 7.23; found: C 58.86, H 5.32, N 6.95.

Methods of Treatment

In order to use a compound of Formula (I) or (II) or a pharmaceutically acceptable salt thereof for the treatment of humans and other mammals, it is normally formulated in accordance with standard pharmaceutical practice as a pharmaceutical composition.

The compounds of Formula (I) or (II), or a pharmaceutically acceptable salt thereof can be used in the manufacture of a medicament for the prophylatic or therapeutic treatment of any disease state in a human or other mammal which is mediated by inhibition of PDE IV, such as but not limited to asthma, allergic, or inflammatory diseases. The compounds of Formula (I) or (II) are administered in an amount sufficient to treat such a disease in a human or other mammal.

For the purposes herein all methods of treatment and dosage regimens apply equally o both the compounds of Formula (I) or (II).

In order to use a compound of Formula (I) or (II), or a pharmaceutically acceptable salt thereof for the treatment of humans and other mammals, it is normally formulated in accordance with standard pharmaceutical practice as a pharmaceutical composition.

The amount of a compound of Formula (I) or (II) required for therapeutic effect on topical administration will, of course, vary with the compound chosen, the nature and severity of the condition and the animal undergoing treatment, and is ultimately at the discretion of the physician.

The daily dosage regimen for oral administration is suitably about 0.001 mg/kg to 100 mg/kg, preferably 0.01 mg/Kg to 40 mg/Kg, of a compound of Formula (I) or a pharmaceutically acceptable salt thereof calculated as the free base. The active ingredient may be administered from 1 to 6 times a day, sufficient to exhibit activity.

No toxic effects are expected when these compounds are administered in accordance with the present invention.

UTILITY EXAMPLES

Example A

Inhibitory effect of compounds of Formula (I) or (II) on in vitro TNF production by human monocytes The inhibitory effect of compounds of Formula (I) or (II) on in vitro TNF production by human monocytes may be determined by the protocol as described in Badger et al., EPO published Application 0 411 754 A2, Feb. 6, 1991, and in Hanna, WO 90/15534, Dec. 27, 1990.

Example B

Two models of endotoxic shock have been utilized to determine in vivo TNF activity for the compounds of Formula (I) or (II). The protocol used in these models is described in Badger et al., EPO published Application 0 411 754 A2, Feb. 6, 1991, and in Hanna, WO 90/15534, Dec. 27, 1990.

The compound of Example 1 herein demonstrated a positive in vivo response in reducing serum levels of TNF induced by the injection of endotoxin.

Example C

Isolation of PDE Isozymes

The phosphodiesterase inhibitory activity and selectivity of the compounds of Formula (I) or (II) can be determined using a battery of five distinct PDE isozymes. The tissues used as sources of the different isozymes are as follows: 1) PDE Ib, porcine aorta; 2) PDE Ic, guinea-pig heart; 3) PDE III, guinea-pig heart; 4) PDE IV, human monocyte; and 5) PDE V (also called "Ia"), canine trachealis. PDEs Ia, Ib, Ic and III are partially purified using standard chromatographic techniques [Torphy and Cieslinski, Mol. Pharmacol., 37:206–214, 1990]. PDE IV is purified to kinetic homogeneity by the sequential use of anion-exchange followed by heparin-Sepharose chromatography [Torphy et al., J. Biol. Chem., 267:1798–1804, 1992].

Phosphodiesterase activity is assayed as described in the protocol of Torphy and Cieslinski, Mol. Pharmacol., 37:206–214, 1990. Positive $IC_{50}$s in the nanomolar to $\mu M$ range for compounds of the workings examples described herein for Formula (I) or (II) have been demonstrated.

Example D

The ability of selected PDE IV inhibitors to increase cAMP accumulation in intact tissues is assessed using U-937 cells, a human monocyte cell line that has been shown to contain a large amount of PDE IV. To assess the activity of PDE IV inhibition in intact cells, nondifferentiated U-937 cells (approximately $10^5$ cells/reaction tube) were incubated with various concentrations (0.01–1000 $\mu M$) of PDE inhibitors for one minute and 1 $\mu M$ prostaglandin E2 for an additional four minutes. Five minutes after initiating the reaction, cells were lysed by the addition of 17.5% perchloric acid, the pH was neutralized by the addition of 1M potassium carbonate and cAMP content was assessed by RIA. A general protocol for this assay is described in Brooker et al., Radioimmunassay of cyclic AMP and cyclic GMP., Adv. Cyclic Nucleotide Res., 10:1–33, 1979. The compounds of the working examples as described herein for Formula (I) or (II) have demonstrated a positive $EC_{50}$s in the $\mu M$ range in the above assay.

What is claimed is:

1. It A compound of formula (I):

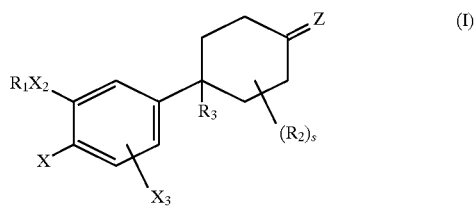

wherein:

$R_1$ is —$(CR_4R_5)_rR_6$ wherein the alkyl moieties may be optionally substituted with one or more halogens;

r is 0;

$R_4$ and $R_5$ are independently selected hydrogen or $C_{1-2}$ alkyl;

$R_6$ is hydrogen, methyl, aryl, substituted aryl, aryloxy$C_{1-3}$ alkyl, halo substituted aryloxy$C_{1-3}$ alkyl, indanyl, indenyl, $C_{7-11}$ polycycloalkyl, tetrahydrofuranyl, furanyl, tetrahydropyranyl, pyranyl, tetrahydrothienyl, thienyl, tetrahydrothiopyranyl, thiopyranyl, $C_{3-6}$ cycloalkyl, or a $C_{4-6}$ cycloalkyl containing one or two unsaturated bonds, wherein the cycloalkyl and heterocyclic moieties may be optionally substituted by 1 to 3 methyl groups or one ethyl group;

X is $YR_2$, halogen, nitro, $NR_4R_5$, or formyl amine;

Y is O or S(O)$_{m'}$;
m' is 0, 1, or 2;

X$_2$ is O or NR$_8$;

X$_3$ is hydrogen or X;

R$_2$ is independently selected from —CH$_3$ or —CH$_2$CH$_3$ optionally substituted by 1 or more halogens;

s is 0 to 4;

R$_3$ is CN;

Z' is O, NR$_9$, NOR$_8$, NCN, C(—CN)$_2$, CR$_8$CN, CR$_8$NO$_2$, CR$_8$C(O)OR$_8$, CR$_8$C(O)NR$_8$R$_8$, C(—CN)NO$_2$, C(—CN)C(O)OR$_9$, or C(—CN)C(O)NR$_8$R$_8$;

Z is O, NR$_7$, NCR$_4$R$_5$C$_{2-6}$ alkenyl, NOR$_{14}$, NOR$_{15}$, NOCR$_4$R$_5$C$_{2-6}$ alkenyl, NNR$_4$R$_{14}$, NNR$_4$R$_{15}$, NCN, NNR$_8$C(O)NR$_8$R$_{14}$, NNR$_8$C(S)NR$_8$R$_{14}$, or =Z is 2-(1,3-dithiane), 2-(1,3-dithilolane), dimethylthio ketal, diethylthio ketal, 2-(1,3-dioxolane), 2(1,3-dioxane), 2-(1,3-oxathiolane), dimethyl ketal or diethyl ketal;

R$_7$ is —(CR$_4$R$_5$)$_q$R$_{12}$ or C$_{1-6}$ alkyl wherein the R$_{12}$ or C$_{1-6}$ alkyl group is optionally substituted one or more times by C$_{1-2}$ alkyl optionally substituted by one to three fluorines, —F, —Br, —Cl, —NO$_2$, —Si(R$_4$)$_3$, —NR$_{10}$R$_{11}$, —C(O)R$_8$, —CO$_2$R$_8$, —OR$_8$, —CN, —C(O)NR$_{10}$R$_{11}$, —OC(O)NR$_{10}$R$_{11}$, —OC(O)R$_8$, —NR$_{10}$C(O)NR$_{10}$R$_{11}$, —NR$_{10}$C(O)R$_{11}$, —NR$_{10}$C(O)OR$_9$, —NR$_{10}$C(O)R$_{13}$, —C(NR$_{10}$)NR$_{10}$R$_{11}$, —C(NCN)NR$_{10}$R$_{11}$, —C(NCN)SR$_9$, —NR$_{10}$C(NCN)SR$_9$, —NR$_{10}$C(NCN)NR$_{10}$R$_{11}$, —NR$_{10}$S(O)$_2$R$_9$, —S(O)$_m$R$_9$, —NR$_{10}$C(O)C(O)NR$_{10}$R$_{11}$, —NR$_{10}$C(O)C(O)R$_{10}$, thiazolyl, imidazolyl, oxazolyl, pyrazolyl, triazolyl, or tetrazolyl;

q is 0, 1, or 2;

R$_{12}$ is C$_{3-7}$ cycloalkyl, (2-, 3- or 4-pyridyl), pyrimidyl, pyrazolyl, (1- or 2-imidazolyl), thiazolyl, triazolyl, pyrrolyl, piperazinyl, piperidinyl, morpholinyl, furanyl, (2- or 3-thienyl), (4- or 5-thiazolyl), quinolinyl, naphthyl, or phenyl;

R$_8$ is independently selected from hydrogen or R$_9$;

R$_{8'}$ is R$_8$ or fluorine;

R$_9$ is C$_{1-4}$ alkyl optionally substituted by one to three fluorines;

R$_{10}$ is OR$_8$ or R$_{11}$;

R$_{11}$ is hydrogen, or C$_{1-4}$ alkyl optionally substituted by one to three fluorines; or when R$_{10}$ and R$_{11}$ are as NR$_{10}$R$_{11}$ they may together with the nitrogen form a 5 to 7 membered ring optionally containing at least one additional heteroatom selected from O, N, or S;

R$_{13}$ is oxazolidinyl, oxazolyl, thiazolyl, pyrazolyl, triazolyl, tetrazolyl, imidazolyl, imidazolidinyl, thiazolidinyl, isoxazolyl, oxadiazolyl, or thiadiazolyl, and each of these heterocyclic rings is connected through a carbon atom and each may be unsubstituted or substituted by one or two C$_{1-2}$ alkyl groups;

R$_{14}$ is hydrogen or R$_7$; or when R$_8$ and R$_{14}$ are as NR$_8$R$_{14}$ they may together with the nitrogen form a 5 to 7 membered ring optionally containing one or more additional heteroatoms selected from O, N, or S;

R$_{15}$ is C(O)R$_{14}$, C(O)NR$_4$R$_{14}$, S(O)$_2$R$_7$, or S(O)$_2$NR$_4$R$_{14}$;

provided that:

(a) when R$_{12}$ is N-pyrazolyl, N-imidazolyl, N-triazolyl, N-pyrrolyl, N-piperazinyl, N-piperidinyl, or N-morpholinyl, then q is not 1;

(b) when Z is O and X is YR$_2$ where Y is O and R$_2$ is methyl or ethyl and X$_2$ is O, R$_1$ is not methyl;

or the pharmaceutically acceptable salts thereof.

2. A compound of formula (II):

wherein:

R$_1$ is —(CR$_4$R$_5$)$_n$C(O)O(CR$_4$R$_5$)$_m$R$_6$, —(CR$_4$R$_5$)$_n$C(O)NR$_4$(CR$_4$R$_5$)$_m$R$_6$, —(CR$_4$R$_5$)$_n$O(CR$_4$R$_5$)$_m$R$_6$, or —(CR$_4$R$_5$)$_r$R$_6$ wherein the alkyl moieties may be optionally substituted with one or more halogens;

m is 0 to 2;

n is 1 to 4;

r is 0 to 6;

R$_4$ and R$_5$ are independently selected hydrogen or C$_{1-2}$ alkyl;

R$_6$ is hydrogen, methyl, hydroxyl, aryl, halo substituted aryl, aryloxyC$_{1-3}$ alkyl, halo substituted aryloxyC$_{1-3}$ alkyl, indanyl, indenyl, C$_{7-11}$ polycycloalkyl, tetrahydrofuranyl, furanyl, tetrahydropyranyl, pyranyl, tetrahydrothienyl, thienyl, tetrahydrothiopyranyl, thiopyranyl, C$_{3-6}$ cycloalkyl, or a C$_{4-6}$ cycloalkyl containing one or two unsaturated bonds, wherein the cycloalkyl and heterocyclic moieties is unsubstituted or substituted by 1 to 3 methyl groups or one ethyl group;

provided that:

a) when R$_6$ is hydroxyl, then m is 2; or b) when R$_6$ is hydroxyl, then r is 2 to 6; or c) when R$_6$ is 2-tetrahydropyranyl, 2-tetrahydrothiopyranyl, 2-tetrahydrofuranyl, or 2-tetrahydrothienyl, then m is 1 or 2; or d) when R$_6$ is 2-tetrahydropyranyl, 2-tetrahydrothiopyranyl, 2-tetrahydrofuranyl, or 2-tetrahydrothienyl, then r is 1 to 6;

e) when n is 1 and m is 0, then R$_6$ is other than H in —(CR$_4$R$_5$)$_n$O(CR$_4$R$_5$)$_m$R$_6$;

X is YR$_2$, halogen, nitro, NR$_4$R$_5$, or formyl amine;

Y is O or S(O)$_{m'}$;

m' is 0, 1, or 2;

X$_2$ is O or NR$_8$;

X$_3$ is hydrogen or X;

R$_2$ is independently selected from —CH$_3$ or —CH$_2$CH$_3$ optionally substituted by 1 or more halogens;

s is 0 to 4;

R$_3$ is CN;

Z' is O, NR$_9$, NOR$_8$, NNR$_8$R$_8$, NCN, C(—CN)$_2$, CR$_8$CN, CR$_8$NO$_2$, CR$_8$C(O)OR$_9$, CR$_8$C(O)NR$_8$R$_8$, C(—CN)NO$_2$, C(—CN)C(O)OR$_9$, or C(—CN)C(O)NR$_8$R$_8$;

Z" is C(Y')R$_{14}$, C(O)OR$_{14}$, C(Y')NR$_{10}$R$_{14}$, C(NR$_{10}$)NR$_{10}$R$_{14}$, CN, C(NOR$_8$)R$_{14}$, C(O)NR$_8$NR$_8$C(O)R$_8$, C(O)NR$_8$NR$_{10}$R$_{14}$, C(NOR$_{14}$)R$_8$, C(NR$_8$)NR$_{10}$R$_{14}$, C(NR$_{14}$)NR$_8$R$_8$, C(NCN)NR$_{10}$R$_{14}$, C(NCN)SR$_9$, (2-, 4- or 5-imidazolyl), (3-, 4- or 5-pyrazolyl), (4- or 5-triazolyl[1,2,3]), (3- or 5-triazolyl[1,2,4]), (5-tetrazolyl), (2-, 4- or 5-oxazolyl), (3-, 4- or 5-isoxazolyl), (3- or 5-oxadiazolyl[1,2,4]), (2-oxadiazolyl[1,3,4]), (2-thiadiazolyl[1,3,4]), (2-, 4-, or 5-thiazolyl), (2-, 4-, or 5-oxazolidinyl), (2-, 4-, or 5-thiazolidinyl), or (2-, 4-, or 5-imidazolidinyl); wherein all of the heterocylic ring systems may be optionally substituted one or more times by $R_{14}$;

Y' is O or S;

$R_7$ is $—(CR_4R_5)_qR_{12}$ or $C_{1-6}$ alkyl wherein the $R_{12}$ or $C_{1-6}$ alkyl group is optionally substituted one or more times by $C_{1-2}$ alkyl optionally substituted by one to three fluorines, —F, —Br, —Cl, —$NO_2$, —$Si(R_4)_3$, —$NR_{10}R_{11}$, —$C(O)R_8$, —$CO_2R_8$, —$OR_8$, —CN, —$C(O)NR_{10}R_{11}$, —$OC(O)NR_{10}R_{11}$, —$OC(O)R_8$, —$NR_{10}C(O)NR_{10}R_{11}$, —$NR_{10}C(O)R_{11}$, —$NR_{10}C(O)OR_9$, —$NR_{10}C(O)R_{13}$, —$C(NR_{10})NR_{10}R_{11}$, —$C(NCN)NR_{10}R_{11}$, —$C(NCN)SR_9$, —$NR_{10}C(NCN)SR_9$, —$NR_{10}C(NCN)NR_{10}R_{11}$, —$NR_{10}S(O)_2R_9$, —$S(O)_{m'}R_9$, —$NR_{10}C(O)C(O)NR_{10}R_{11}$, —$NR_{10}C(O)C(O)R_{10}$, thiazolyl, imidazolyl, oxazolyl, pyrazolyl, triazolyl, or tetrazolyl;

q is 0, 1, or 2;

$R_{12}$ is $C_{3-7}$ cycloalkyl, (2-, 3- or 4-pyridyl), pyrimidyl, pyrazolyl, (1- or 2-imidazolyl), triazolyl, pyrrolyl, piperazinyl, piperidinyl, morpholinyl, furanyl, (2- or 3-thienyl), (4- or 5-thiazolyl), quinolinyl, naphthyl, or phenyl;

$R_8$ is independently selected from hydrogen or $R_9$;

$R_{8'}$ is $R_8$ or fluorine;

$R_9$ is $C_{1-4}$ alkyl optionally substituted by one to three fluorines;

$R_{10}$ is $OR_8$ or $R_{11}$;

$R_{11}$ is hydrogen, or $C_{1-4}$ alkyl optionally substituted by one to three fluorines; or when $R_{10}$ and $R_{11}$ are as $NR_{10}R_{11}$ they may together with the nitrogen form a 5 to 7 membered ring optionally containing at least one additional heteroatom selected from O, N, or S;

$R_{13}$ is oxazolidinyl, oxazolyl, thiazolyl, pyrazolyl, triazolyl, tetrazolyl, imidazolyl, imidazolidinyl, thiazolidinyl, isoxazolyl, oxadiazolyl, or thiadiazolyl, and each of these heterocyclic rings is connected through a carbon atom and each may be unsubstituted or substituted by one or two $C_{1-2}$ alkyl groups;

$R_{14}$ is hydrogen or $R_7$; or when $R_8$ and $R_{14}$ are as $NR_8R_{14}$ they may together with the nitrogen form a 5 to 7 membered ring optionally containing one or more additional heteroatoms selected from O, N, or S;

$R_{15}$ is $C(O)R_{14}$, $C(O)NR_4R_{14}$, $S(O)_2R_7$, or $S(O)_2NR_4R_{14}$;

provided that:

f) when $R_{12}$ is N-pyrazolyl, N-imidazolyl, N-triazolyl, N-pyrrolyl, N-piperazinyl, N-piperidinyl, or N-morpholinyl, then q is not 1; or g) when Z" is $C(O)OR_{14}$ where $R_{14}$ is lower alkyl and $R_3$ is CN, then $R_1X_2$ is not $C_1$–$C_3$ alkoxy and X is not halogen, methoxy, ethoxy, methylthio, or ethylthio;

or the pharmaceutically acceptable salts thereof.

3. A compound according to claim 1 wherein $R_1$ is $C_{4-6}$ cycloalkyl, $C_{7-11}$ polycycloalkyl, (3- or 4-cyclopentenyl), phenyl, tetrahydrofuran-3-yl, benzyl or $C_{1-2}$ alkyl optionally substituted by —$(CH_2)_{1-3}C(O)O(CH_2)_{0-2}CH_3$, —$(CH_2)_{1-3}O(CH_2)_{0-2}CH_3$, —$(CH_2)_{2-4}OH$, or 2 or more fluorines;

X is $YR_2$, halogen, nitro, $NR_4R_5$, or formyl amine;

Y is O or $S(O)_{m'}$;

m' is 0, 1, or 2;

$X_2$ is O or $NR_8$:

$R_4$ and $R_5$ are independently hydrogen or $C_{1-2}$alkyl;

Z' is O, $NR_9$, $NOR_8$, $NNR_8R_8$, NCN, $C(—CN)_2$, $CR_8CN$, $CR_8NO_2$, $CR_8C(O)OR_9$, $CR_8C(O)NR_8R_8$, $C(—CN)NO_2$, $C(—CN)C(O)OR_9$, or $C(—CN)C(O)NR_8R_8$;

Z" is $C(Y')R_{14}$, $C(O)OR_{14}$, $C(Y')NR_{10}R_{14}$, $C(NR_{10})NR_{10}R_{14}$, CN, $C(NOR_8)R_{14}$, $C(O)NR_8NR_8C(O)R_8$, $C(O)NR_8NR_{10}R_{14}C(NOR_{14})R_8$, $C(NR_8)NR_{10}R_{14}$, $C(NR_{14})NR_8R_8$ $C(NCN)NR_{10}R_{14}$, $C(NCN)SR_9$, (2-, 4- or 5-imidazolyl), (3-, 4- or 5-pyrazolyl), (4- or 5-triazolyl[1,2,3]), (3- or 5-triazolyl[1,2,4]), (5-tetrazolyl), (2-, 4- or 5-oxazolyl), (3-, 4- or 5-isoxazolyl), (3- or 5-oxadiazolyl[1,2,4]), (2-oxadiazolyl[1,3,4]), (2-thiadiazolyl[1,3,4]), (2-, 4-, or 5-thiazolyl), (2-, 4- or 5-oxazolidinyl), (2-, 4-, or 5-thiazolidinyl), or (2-, 4-, or 5-imidazolidinyl); wherein all of the heterocyclic ring systems may be optionally substituted one or more times by $R_{14}$;

Y' is O or S;

$R_7$ is $—(CR_4R_5)_qR_{12}$ or $C_{1-6}$ alkyl wherein the $R_{12}$ or $C_{1-6}$ alkyl group is optionally substituted one or more times by $C_{1-2}$ alkyl optionally substituted by one to three fluorines, —F, —Br, —Cl, —$NO_2$, —$Si(R_4)_3$, —$NR_{10}R_{11}$, —$C(O)R_8$, —$CO_2R_8$, —$OR_8$, —CN, —$C(O)NR_{10}R_{11}$, —$OC(O)NR_{10}R_{11}$, —$OC(O)R_8$, —$NR_{10}C(O)NR_{10}R_{11}$, —$NR_{10}C(O)R_{11}$, —$NR_{10}C(O)OR_9$, —$NR_{10}C(O)R_{13}$, —$C(NR_{10})NR_{10}R_{11}$, —$C(NCN)NR_{10}R_{11}$, —$C(NCN)SR_9$, —$R_{10}C(NCN)SR_9$, —$NR_{10}C(NCN)NR_{10}R_{11}$, —$NR_{10}S(O)_2R_9$, —$S(O)_{m'}R_9$, —$NR_{10}C(O)C(O)NR_{10}R_{11}$, —$NR_{10}C(O)C(O)R_{10}$, thiazolyl, imidazolyl, oxazolyl, pyrazolyl, triazolyl, or tetrazolyl;

q is 0, 1, or 2;

$R_{12}$ is $C_{3-7}$ cycloalkyl, (2-, 3- or 4-pyridyl), (1- or 2-imidazolyl), piperazinyl, morpholinyl, (2- or 3-thienyl), (4- or 5-thiazolyl), or phenyl;

$R_8$ is independently selected from hydrogen or $R_9$;

$R_{8'}$ is $R_8$ or fluorine;

$R_9$ is $C_{1-4}$ alkyl optionally substituted by one to three fluorines;

$R_{10}$ is $OR_8$ or $R_{11}$;

$R_{11}$ is hydrogen or $C_{1-4}$ alkyl optionally substituted by one to three fluorines; or when $R_{10}$ and $R_{11}$ are as $NR_{10}R_{11}$ they may together with the nitrogen form a 5 to 7 membered ring optionally containing at least one additional heteroatom selected from O, N, or S;

$R_{13}$ is oxazolidinyl, oxazolyl, thiazolyl, pyrazolyl, triazolyl, tetrazolyl, imidazolyl, imidazolidinyl, thiazolidinyl, isoxazolyl, oxadiazolyl, or thiadiazolyl, and each of these heterocyclic rings is connected through a carbon atom and each may be unsubstituted or substituted by one or two $C_{1-2}$ alkyl groups;

$R_{14}$ is hydrogen or $R_7$; or when $R_8$ and $R_{14}$ are as $NR_8R_{14}$ they may together with the nitrogen form a 5 to 7 membered ring optionally containing one or more additional heteroatoms selected from O, N, or S;

provided that:

when $R_{12}$ is N-imidazolyl, N-triazolyl, N-pyrrolyl, N-piperazinyl, or N-morpholinyl, then q is not 1;

or the pharmaceutically acceptable salts thereof.

4. A compound of claim 3 where:

Z is O, NCN, NR$_7$, NOR$_{14}$, NOR$_{15}$, NNR$_4$R$_{14}$, NNR$_4$R$_{15}$, dimethyl ketal or dimethylthio ketal;

X is YR$_2$ and Y is oxygen;

R$_2$ is methyl, —CF$_3$, —CHF$_2$, or —CH$_2$CHF$_2$;

Z" is O or NOR$_8$;

R$_7$ is unsubstituted or substituted —(CH$_2$)$_{1-2}$(cyclopropyl), —(CH$_2$)$_{0-2}$(cyclobutyl), —(CH$_2$)$_{0-2}$(cyclopentyl), —(CH$_2$)$_{0-2}$(cyclohexyl), —(CH$_2$)$_{0-2}$(2-, 3- or 4-pyridyl), (CH$_2$)$_{1-2}$(2-imidazolyl), (CH$_2$)$_2$(4-morpholinyl), (CH$_2$)$_2$(4-piperazinyl), (CH$_2$)$_{1-2}$(2-thienyl), (CH$_2$)$_{1-2}$(4-thiazolyl), and (CH$_2$)$_{0-2}$phenyl;

when R$_{10}$ and R$_{11}$ in the moiety —NR$_{10}$R$_{11}$ together with the nitrogen to which they are attached form a 5 to 7 membered ring it is 1-imidazolyl, 2-(R$_8$)-1-imidazolyl, 1-pyrazolyl, 3-(R$_8$)-1-pyrazolyl, 1-triazolyl, 2-triazolyl, 5-(R$_8$)-1-triazolyl, 5-(R$_8$)-2-triazolyl, 5-(R$_8$)-1-tetrazolyl, 5-(R$_8$)-2-tetrazolyl, 1-tetrazolyl, 2-tetrazloyl, morpholinyl, piperazinyl, 4-(R$_8$)-1-piperazinyl, or pyrrolyl;

when R$_8$ and R$_{14}$ in the moiety —NR$_8$R$_{14}$ together with the nitrogen to which they are attached may form a 5 to 7 membered ring it is 1-imidazolyl, 1-pyrazolyl, 1-triazolyl, 2-triazolyl, 1-tetrazolyl, 2-tetrazolyl, morpholinyl, piperazinyl, and pyrrolyl; wherein each ring may be substituted on an available nitrogen or carbon by R$_7$ which is 2-(R$_7$)-1-imidazolyl, 4-(R$_7$)-1-imidazolyl, 5-(R$_7$)-1-imidazolyl, 3-(R$_7$)-1-pyrazolyl,4-(R$_7$)-1-pyrazolyl, 5-(R$_7$)-1-pyrazolyl, 4-(R$_7$)-2-triazolyl, 5-(R$_7$)-2-triazolyl, 4-(R$_7$)-1-triazolyl, 5-(R$_7$)-1-triazolyl, 5-(R$_7$)-1-tetrazolyl, and 5-(R$_7$)-2-tetrazolyl; and R$_{13}$ is (2-, 4- or 5-imidazolyl), (3-, 4- or 5-pyrazolyl), (4- or 5-triazolyl[1,2,3]), (3- or 5-triazolyl[1,2,4]), (5-tetrazolyl), (2-, 4- or 5-oxazolyl), (3-, 4- or 5-isoxazolyl), (3- or 5-oxadiazolyl[1,2,4]), (2-oxadiazolyl[1,3,4]), (2-thiadiazolyl[1,3,4]), (2-, 4-, or 5-thiazolyl), (2-, 4-, or 5-oxazolidinyl), (2-, 4-, or 5-thiazolidinyl), or (2-, 4-, or 5-imidazolidinyl).

5. A compound according to claim 4 wherein R$_1$ is CH$_2$-cyclopropyl,C$_2$—C$_{5-6}$ cycloalkyl, C$_{4-6}$ cycloalkyl or (3- or 4-cyclopentenyl); R$_2$ is methyl; and Z is O.

6. A compound according to claim 2 wherein

R$_1$ is CH$_2$-cyclopropyl, CH$_2$—C$_{5-6}$ cycloalkyl, C$_{4-6}$ cycloalkyl, C$_{7-11}$ polycycloalkyl, (3- or 4-cyclopentenyl), phenyl, tetrahydrofuran-3-yl, benzyl or C$_{1-2}$ alkyl optionally substituted by —(CH$_2$)$_{1-3}$C(O)O(CH$_2$)$_{0-2}$CH$_3$, —(CH$_2$)$_{1-3}$O(CH$_2$)$_{0-2}$CH$_3$, —(CH$_2$)$_{2-4}$OH, or 2 or more fluorines;

X is YR$_2$, halogen, nitro, NR$_4$R$_5$, or formyl amine;

Y is O or S(O)$_{m'}$;

m' is 0, 1, or 2;

X$_2$ is O or NR$_8$;

R$_4$ and R$_5$ are independently hydrogen or C$_{1-2}$alkyl;

Z' is O, NR$_9$, NOR$_8$, NNR$_8$R$_8$, NCN, C(—CN)$_2$, CR$_8$CN, CR$_8$NO$_2$, CR$_8$C(O)OR$_9$, CR$_8$C(O)NR$_8$R$_8$, C(—CN)NO$_2$, C(—CN)C(O)OR$_9$, or C(—CN)C(O)NR$_8$R$_8$;

Z" is C(Y')R$_{14}$, C(O)OR$_{14}$, C(Y')NR$_{10}$R$_{14}$, C(NR$_{10}$)NR$_{10}$R$_{14}$, CN, C(NOR$_8$)R$_{14}$, C(O)NR$_8$NR$_8$C(O)R$_8$, C(O)NR$_8$NR$_{10}$R$_{14}$, C(NOR$_{14}$)R$_8$, C(NR$_8$)NR$_{10}$R$_{14}$, C(NR$_{14}$)NR$_8$R$_8$ C(NCN)NR$_{10}$R$_{14}$, C(NCN)SR$_9$, (2-, 4- or 5-imidazolyl), (3-, 4- or 5-pyrazolyl), (4- or 5-triazolyl[1,2,3]), (3- or 5-triazolyl[1,2,4]), (5-tetrazolyl), (2-, 4- or 5-oxazolyl), (3-, 4- or 5-isoxazolyl), (3- or 5-oxadiazolyl[1,2,4]), (2-oxadiazolyl[1,3,4]), (2-thiadiazolyl[1,3,4]), (2-, 4-, or 5-thiazolyl), (2-, 4-, or 5-oxazolidinyl), (2-, 4-, or 5-thiazolidinyl), or (2-, 4-, or 5-imidazolidinyl); wherein all of the heterocyclic ring systems may be optionally substituted one or more times by R$_{14}$;

Y' is O or S;

R$_7$ is —(CR$_4$R$_5$)$_q$R$_{12}$ or C$_{1-6}$ alkyl wherein the R$_{12}$ or C$_{1-6}$ alkyl group is optionally substituted one or more times by C$_{1-2}$ alkyl optionally substituted by one to three fluorines, —F, —Br, —Cl, —NO$_2$, —Si(R$_4$)$_3$, —NR$_{10}$R$_{11}$, —C(O)R$_8$, —CO$_2$R$_8$, —OR$_8$, —CN, —C(O)NR$_{10}$R$_{11}$, —OC(O)NR$_{10}$R$_{11}$, —OC(O)R$_8$, —NR$_{10}$C(O)NR$_{10}$R$_{11}$, —NR$_{10}$C(O)R$_{11}$, —NR$_{10}$C(O)OR$_9$, —NR$_{10}$C(O)R$_{13}$, —C(NR$_{10}$)NR$_{10}$R$_{11}$, —C(NCN)NR$_{10}$R$_{11}$, —C(NCN)SR$_9$, —NR$_{10}$C(NCN)SR$_9$, —NR$_{10}$C(NCN)NR$_{10}$R$_{11}$, —NR$_{10}$S(O)$_2$R$_9$, —S(O)$_m$R$_9$, —NR$_{10}$C(O)C(O)NR$_{10}$R$_{11}$, —NR$_{10}$C(O)C(O)R$_{10}$, thiazolyl, imidazolyl, oxazolyl, pyrazolyl, triazolyl, or tetrazolyl;

q is 0, 1, or 2;

R$_{12}$ is C$_{3-7}$ cycloalkyl, (2-, 3- or 4-pyridyl), (1- or 2-imidazolyl), piperazinyl, morpholinyl, (2- or 3-thienyl), (4- or 5-thiazolyl), or phenyl;

R$_8$ is independently selected from hydrogen or R$_9$;

R$_{8'}$ is R$_8$ or fluorine;

R$_9$ is C$_{1-4}$ alkyl optionally substituted by one to three fluorines;

R$_{10}$ is OR$_8$ or R$_{11}$;

R$_{11}$ is hydrogen or C$_{1-4}$ alkyl optionally substituted by one to three fluorines; or when R$_{10}$ and R$_{11}$ are as NR$_{10}$R$_{11}$ they may together with the nitrogen form a 5 to 7 membered ring optionally containing at least one additional heteroatom selected from O, N, or S;

R$_{13}$ is oxazolidinyl, oxazolyl, thiazolyl, pyrazolyl, triazolyl, tetrazolyl, imidazolyl, imidazolidinyl, thiazolidinyl, isoxazolyl, oxadiazolyl, or thiadiazolyl, and each of these heterocyclic rings is connected through a carbon atom and each may be unsubstituted or substituted by one or two C$_{1-2}$ alkyl groups;

R$_{14}$ is hydrogen or R$_7$; or when R$_8$ and R$_{14}$ are as NR$_8$R$_{14}$ they may together with the nitrogen form a 5 to 7 membered ring optionally containing one or more additional heteroatoms selected from O, N, or S;

provided that:

when R$_{12}$ is N-imidazolyl, N-triazolyl, N-pyrrolyl, N-piperazinyl, or N-morpholinyl, then q is not 1;

or the pharmaceutically acceptable salts thereof.

7. A compound of claim 6 where:

Z is O, NCN, NR$_7$, NOR$_{14}$, NOR$_{15}$, NNR$_4$R$_{14}$, NNR$_4$R$_{15}$, dimethyl ketal or dimethylthio ketal;

X is YR$_2$ and Y is oxygen;

R$_2$ is methyl, —CF$_3$, —CHF$_2$, or —CH$_2$CHF$_2$;

Z' is O or NOR$_8$;

R$_7$ is unsubstituted or substituted —(CH$_2$)$_{1-2}$(cyclopropyl), —(CH$_2$)$_{0-2}$(cyclobutyl), —(CH$_2$)$_{0-2}$(cyclopentyl), —(CH$_2$)$_{0-2}$(cyclohexyl), —(CH$_2$)$_{0-2}$(2-, 3- or 4-pyridyl), (CH$_2$)$_{1-2}$(2-imidazolyl), (CH$_2$)$_2$(4-morpholinyl), (CH$_2$)$_2$(4-piperazinyl), (CH$_2$)$_{1-2}$(2-thienyl), (CH$_2$)$_{1-2}$(4-thiazolyl), and (CH$_2$)$_{0-2}$phenyl;

when R$_{10}$ and R$_{11}$ in the moiety —NR$_{10}$R$_{11}$ together with the nitrogen to which they are attached form a 5 to 7 membered ring it is 1-imidazolyl, 2-(R$_8$)-1-imidazolyl, 1-pyrazolyl, 3-($R_8$)-1-pyrazolyl, 1-triazolyl, 2-triazolyl, 5-($R_8$)-1-triazolyl, 5-($R_8$)-2-triazolyl, 5-($R_8$)-1-tetrazolyl, 5-($R_8$)-2-tetrazolyl, 1-tetrazolyl, 2-tetrazloyl, morpholinyl, piperazinyl, 4-($R_8$)-1-piperazinyl, or pyrrolyl;

when $R_8$ and $R_{14}$ in the moiety —$NR_8R_{14}$ together with the nitrogen to which they are attached may form a 5 to 7 membered ring it is 1-imidazolyl, 1-pyrazolyl, 1-triazolyl, 2-triazolyl, 1-tetrazolyl, 2-tetrazolyl, morpholinyl, piperazinyl, and pyrrolyl; wherein each ring may be substituted on an available nitrogen or carbon by $R_7$ which is 2-($R_7$)-1-imidazolyl, 4-($R_7$)-1-imidazolyl, 5-($R_7$)-1-imidazolyl, 3-($R_7$)-1-pyrazolyl, 4-($R_7$)-1-pyrazolyl, 5-($R_7$)-1-pyrazolyl, 4-($R_7$)-2-triazolyl, 5-($R_7$)-2-triazolyl, 4-($R_7$)-1-triazolyl, 5-($R_7$)-1-triazolyl, 5-($R_7$)-1-tetrazolyl, and 5-($R_7$)-2-tetrazolyl; and $R_{13}$ is (2-, 4- or 5-imidazolyl), (3-, 4- or 5-pyrazolyl), (4- or 5-triazolyl[1,2,3]), (3- or 5-triazolyl[1,2,4]), (5-tetrazolyl), (2-, 4- or 5-oxazolyl), (3-, 4- or 5-isoxazolyl), (3- or 5-oxadiazolyl[1,2,4]), (2-oxadiazolyl[1,3,4]), (2-thiadiazolyl[1,3,4]), (2-, 4-, or 5-thiazolyl), (2-, 4-, or 5-oxazolidinyl), (2-, 4-, or 5-thiazolidinyl), or (2-4-, or 5-imidazolidinyl).

8. A compound according to claim 7 wherein $R_1$ is $CH_2$-cyclopropyl, $CH_2$—$C_{5-6}$ cycloalkyl, $C_{4-6}$ cycloalkyl or 3- or 4-cyclopentenyl; $R_2$ is methyl; and Z is O.

9. A pharmaceutical composition comprising an effective amount of a compound according to claim 1 and a pharmaceutically acceptable excipient.

10. A pharmaceutical composition comprising an effective amount of a compound according to claim 2 and a pharmaceutically acceptable excipient.

* * * * *

UNITED STATES PATENT AND TRADEMARK OFFICE
CERTIFICATE OF CORRECTION

PATENT NO. : 5,811,455
DATED : 22 September 1998
INVENTOR(S) : Christensen, et al.

It is certified that error appears in the above-identified patent and that said Letters Patent is hereby corrected as shown below:

In claim 1 delete the group Z' in column 39, lines 9-11.

In claim 2 delete the group Z' in column 40, lines 56-58.

In claim 3 delete the groups Z' and Z" in column 42, lines 6-19.

In claim 4 delete the group Z" in column 43, line 5.

In claim 6 delete the groups Z' and Z" in column 43, lines 56 bridging column 44, line 4.

In claim 7 delete the group Z in column 44 at lines 53-54 and the group Z" in column 44, line 57.

Signed and Sealed this

Twenty-eighth Day of November, 2000

Attest:

Attesting Officer

Q. TODD DICKINSON

Director of Patents and Trademarks